United States Patent
Perriello et al.

(10) Patent No.: US 7,530,990 B2
(45) Date of Patent: *May 12, 2009

(54) ENDOBUTTON CONTINUOUS LOOP FOR BONE TENDON WITH DOUBLE LOOP KNOT

(75) Inventors: Michael Perriello, Hopedale, MA (US); Stuart E. Fromm, Rapid City, SD (US)

(73) Assignee: Smith & Nephew, Inc., Memphis, TN (US)

( * ) Notice: Subject to any disclaimer, the term of this patent is extended or adjusted under 35 U.S.C. 154(b) by 697 days.

This patent is subject to a terminal disclaimer.

(21) Appl. No.: 10/895,266

(22) Filed: Jul. 20, 2004

(65) Prior Publication Data

US 2005/0038427 A1 Feb. 17, 2005

Related U.S. Application Data

(63) Continuation-in-part of application No. 10/391,457, filed on Mar. 18, 2003, now abandoned, which is a continuation of application No. 09/859,096, filed on May 16, 2001, now Pat. No. 6,533,802.

(51) Int. Cl.
*A61B 17/04* (2006.01)
*A61F 2/08* (2006.01)

(52) U.S. Cl. .............. 606/232; 606/72; 623/13.11

(58) Field of Classification Search .......... 606/232, 606/72, 103, 151; 623/13.11, 13.13, 13.14
See application file for complete search history.

(56) References Cited

U.S. PATENT DOCUMENTS

| | | | |
|---|---|---|---|
| 3,880,166 A | 4/1975 | Fogarty | |
| 4,823,794 A | 4/1989 | Pierce | |
| 5,139,520 A | 8/1992 | Rosenberg | |
| 5,306,301 A | 4/1994 | Graf et al. | |
| 5,405,352 A * | 4/1995 | Weston | 606/148 |
| 5,628,756 A * | 5/1997 | Barker et al. | 606/139 |
| 5,645,588 A | 7/1997 | Graf et al. | |
| 5,693,060 A | 12/1997 | Martin | |
| 5,733,289 A | 3/1998 | Seedhom et al. | |
| 5,769,894 A | 6/1998 | Ferragamo | |
| 5,782,864 A | 7/1998 | Lizardi | |
| 6,056,752 A | 5/2000 | Roger | |
| 6,080,154 A * | 6/2000 | Reay-Young et al. | 606/60 |
| 6,086,591 A | 7/2000 | Bojarski | |
| 6,110,207 A | 8/2000 | Eichhorn et al. | |
| 6,517,578 B2 * | 2/2003 | Hein | 623/13.13 |

(Continued)

FOREIGN PATENT DOCUMENTS

EP 0 598 219 A2 5/1994

(Continued)

*Primary Examiner*—Julian W. Woo
*Assistant Examiner*—Katherine Dowe
(74) *Attorney, Agent, or Firm*—Fish & Richardson P.C.

(57) ABSTRACT

A method of securing a tissue graft within a bone passage includes providing a graft fixation member comprising a closed double-loop having a pair of differently sized loop sections and capturing both sections of the closed-loop within the fixation member. The longer loop section is passed through an opening in the tissue graft then is passed through the smaller loop and thrown over the fixation member to form a knot.

10 Claims, 25 Drawing Sheets

U.S. PATENT DOCUMENTS

| | | | |
|---|---|---|---|
| 6,533,802 B2 * | 3/2003 | Bojarski et al. | 606/232 |
| 7,077,863 B2 * | 7/2006 | Schmieding et al. | 623/13.14 |
| 2002/0161439 A1 | 10/2002 | Strobel et al. | |
| 2005/0065533 A1 * | 3/2005 | Magen et al. | 606/102 |
| 2006/0064126 A1 * | 3/2006 | Fallin et al. | 606/232 |

FOREIGN PATENT DOCUMENTS

| | | |
|---|---|---|
| WO | WO98/12991 | 4/1998 |
| WO | WO 98/12992 | 4/1998 |
| WO | WO99/47079 | 9/1999 |
| WO | WO 01/91670 | 12/2001 |
| WO | WO 02/32345 | 4/2002 |

* cited by examiner

ENDOBUTTON CONTINUOUS LOOP FOR BONE TENDON WITH DOUBLE LOOP KNOT

This application is a continuation-in-part and claims the benefit of the U.S. application Ser. No. 10/391,457, filed Mar. 18, 2003 now abandoned, which is a continuation of U.S. application Ser. No. 09/859,096, filed May 16, 2001, which is now U.S. Pat. No. 6,533,802.

BACKGROUND OF THE INVENTION

An increasing number of surgical techniques are now performed arthroscopically. One type of arthroscopic procedure reconstructs the anterior cruciate ligament (ACL) in the knee. Several ACL reconstruction techniques are described in U.S. Pat. No. 5,139,520 (issued Aug. 18, 1992, known herein as "the '520 patent") and incorporated by reference.

A substitute graft harvested from the patient or from a donor usually replaces an ACL that has ruptured and is non-repairable. The substitute ACL graft may be a portion of a patellar tendon having so called "bone blocks" at each end. A method and an apparatus for harvesting such a patellar tendon graft is described in U.S. Pat. No. 5,733,289 (issued Mar. 31, 1998, known herein as "the '289 patent") and incorporated by reference. Alternatively, an artificial graft formed from synthetic materials or from a combination of artificial and natural materials may be used and is sometimes referred to as a ligament augmentation device (LAD). The term "tissue graft" is used herein to encompass all of these tissue replacement items.

In general, the replacement tissue graft is implanted by securing one end of the tissue graft in a socket formed in a passage formed within the femur (i.e. femoral channel) and passing the other end of the graft through a passage formed in the tibia (i.e. tibial channel). The graft is then secured to the tibia adjacent to the tibial channel. Generally, sutures are used to affix each end of the tissue graft to a fastener (e.g. an interference screw or a post), which is then secured to the bone. Descriptions of these fasteners and methods of forming the passages through the tibia and femur are described in greater detail in the '520 patent.

Another approach for affixing a tissue graft is described in U.S. Pat. No. 5,306,301 (issued Apr. 26, 1994, known herein as "the '301 patent") and incorporated by reference. The '301 patent discloses using a fixation button to secure a tissue graft at the femoral cortex. The fixation button has an elongated shape and at least one pair of openings through which a suture may be passed and then tied off.

In this approach, the femoral channel has a portion having a first diameter sized to accommodate a bone block and a second portion having a smaller diameter through which the bone block cannot pass. By measuring the total length of the femoral channel and the length of the larger portion, the surgeon determines a "suture span" for attaching the fixation button to the tissue graft.

The surgeon forms an opening in the bone block to be positioned in the femoral channel and threads an end of suture through it. The surgeon then ties the suture to the fixation button, providing the suture span between the button and the bone block. The fixation button and the tissue graft are then passed through the tibial and femoral channels until the graft is properly seated within the socket portion of the femoral passage and the fixation button is firmly seated against the femoral cortex. The tissue graft is then tensioned and anchored at its opposite end using a fixation screw secured within the tibia.

Still another approach for affixing a tissue graft is described in U.S. Pat. No. 5,769,894 (issued Jun. 23, 1998, known herein as "the '894 patent") and incorporated by reference. The '894 patent describes a graft fixation member configured to allow the length of the suture between the fixation member and the graft to be adjusted and to maintain the adjusted length when the suture is secured to the graft fixation member.

An alternative to tying a suture to a fixation button is disclosed in PCT Application WO 99/47079 (published Sep. 23, 1999, known herein as "the '079 application") and incorporated by reference. The '079 application discloses an apparatus and method for attaching a continuous loop of suture to a fixation button. Using a series of rollers, the continuous loop is formed from a strand of suture repeatedly coiling the suture through openings in a fixation button. In other examples, a continuous loop of suture may be formed without a fixation member. Continuous loops, both with and without fixation buttons attached, are available from Xiros Limited, Leeds, England, in several sizes. A surgeon selects the closest matching size for a given ACL reconstruction procedure. In other examples, a continuous loop of suture may be formed without a fixation member.

SUMMARY OF THE INVENTION

In one aspect of the invention, a method for securing a tissue graft within a bone passage includes providing a graft fixation member comprising a closed double-loop having a pair of loop sections. The first one of the pair of loop sections is passed through an opening in the tissue graft and is secured to the fixation member through a knotting technique with the second one of the pair of loop sections and the graft fixation member. The knotting technique is achieved by passing the first of the pair through the second of the pair and positioned over the fixation member. The fixation member is pulled from the bone block to form the knot.

One or more of the following features may also be included. The opening is formed in the tissue graft. The opening is formed in a bone block of the tissue graft. The opening is formed in a tendon of the tissue graft. The fixation member is passed through the bone passage. The fixation member is passed through a bone passage in a tibia and then through a bone passage in a femur. The fixation member is first passed through a bone passage in a femur and then through a bone passage in a tibia. The fixation member is positioned to pass through the bone passage using a suture. The fixation member is positioned to pass through the bone passage using closure tape.

One or more openings pass through the intermediate portion of the member. The openings are cylindrical. The opening in each arm is cylindrical. The openings in each pair of arms occupy different positions on a common axis. The axis is transverse to the member. The pair of arms defines a cylindrical portion of the channel having a diameter equal to the width of the channel. Each pair of arms defines a cylindrical portion of the channel having a diameter greater than the width of the channel. The arms are shaped to pass through bone passage. The member is sized to pass through a bone passage. The member comprises a biocompatible material. The member comprises titanium. The member comprises a bioabsorbable material.

Embodiments may have one or more of the following advantages. The closed double-loop evenly distributes the load when the loop is passed through a graft. The closed double-loop may be manufactured and purchased separate from the fixation member. This allows the surgeon the flexibility to choose the correctly sized closed double-loop from several sizes available in the operating room without a fixation member on each size loop. In turn, the patient benefits from the reliability of the closed double-loop without the added cost of multiple fixation members. The closed double-loop is positively captured within the fixation member during implantation. The closed double-loop provides superior strength over single loops of tied suture or tape and does not extend a patient's time under anesthesia while a surgeon forms multiple loops of suture or tape by hand. The closed double-loop may be pre-stressed during the manufacturing process to reduce its elasticity and increase its strength without accommodation for a fixation member.

The details of one or more embodiments of the invention are set forth in the accompanying drawings and the description below. Other features, objects, and advantages of the invention will be apparent from the description and drawings.

DETAILED DESCRIPTION

Figure 1:
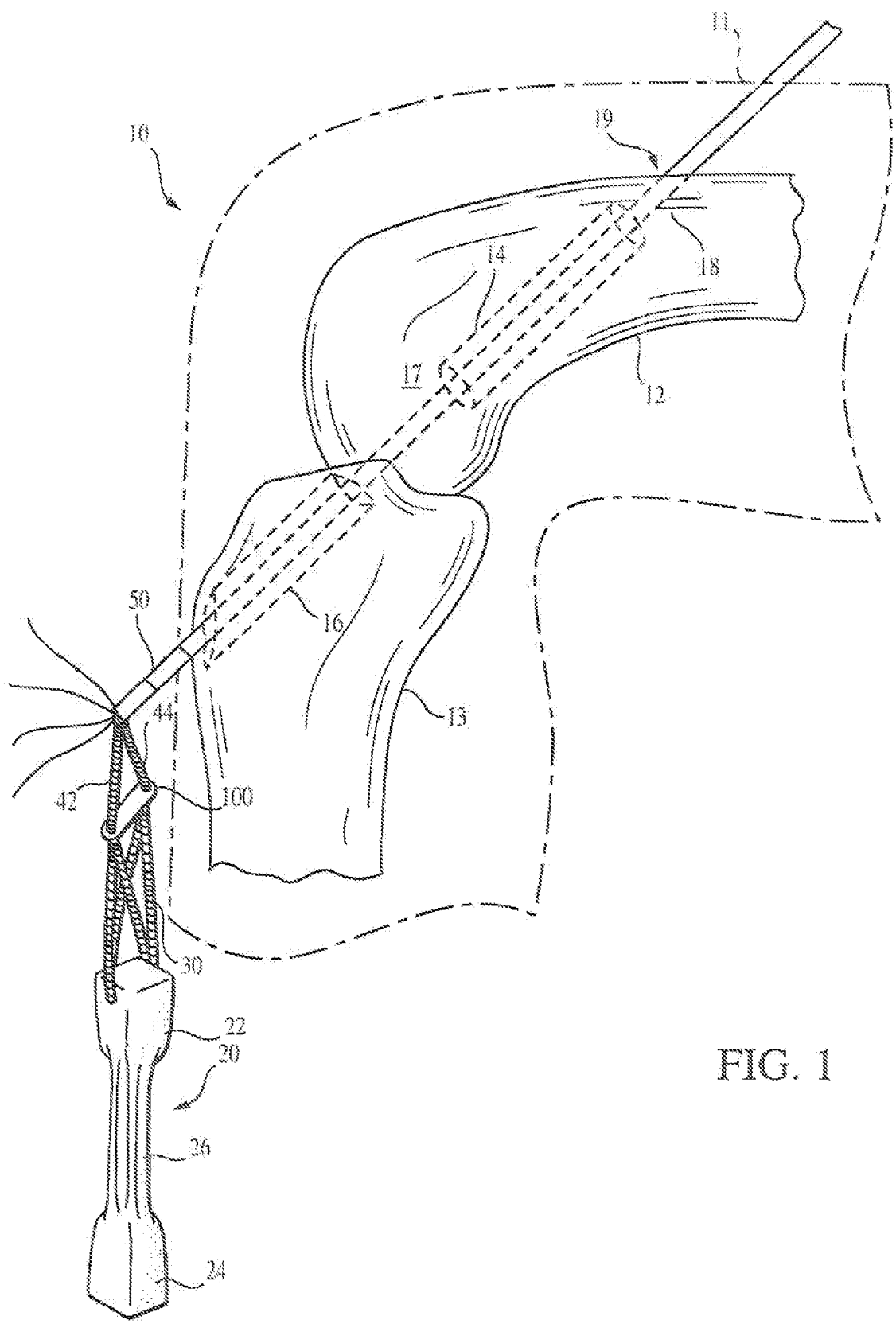
FIG. 1 shows an example of a tissue graft being implanted during an ACL reconstruction procedure using the closed-loop suture and a graft fixation member.

Referring to FIG. 1, a tissue graft 20 is shown being implanted within a knee 10 during an anterior cruciate ligament (ACL) repair and reconstruction procedure. In one example, tissue graft 20 has bone blocks on both ends sized and shaped to fit within femoral and tibial channels, respectively. More specifically, one end of tissue graft 20 includes a bone block 22 shaped and sized in substantial conformity with a femoral channel 14 of femur 12 while the other end of tissue graft 20 includes a bone block 24 shaped and sized in substantial conformity with tibial channel 16 of tibia 13. In one example, a closed-loop suture 30 is inserted into bone block 24 and captured within graft fixation member 100. Closed-loop suture 30 could be, but is not limited to, a Smith & Nephew continuous loop made from polyester, a strand of suture tied in a loop, or a piece of polyester closure tape (e.g. Marselene™ from Ethicon Inc., Cincinnati, Ohio) tied in a loop. As will be described below, graft fixation member 100 is configured to facilitate positioning and securing the tissue graft 20.

Sutures 42 and 44 extend through fixation member 100 and are removably attached to passing pin 50 which is used to draw the sutures 42, 44 through the tibial channel 16, femoral channel 14, and passing channel 18. As described below, sutures 42, 44 are used to pull graft fixation member 100 through passing channel 18 and position tissue graft 20 within femoral channel 14 and tibial channel 16.

Figure 2:
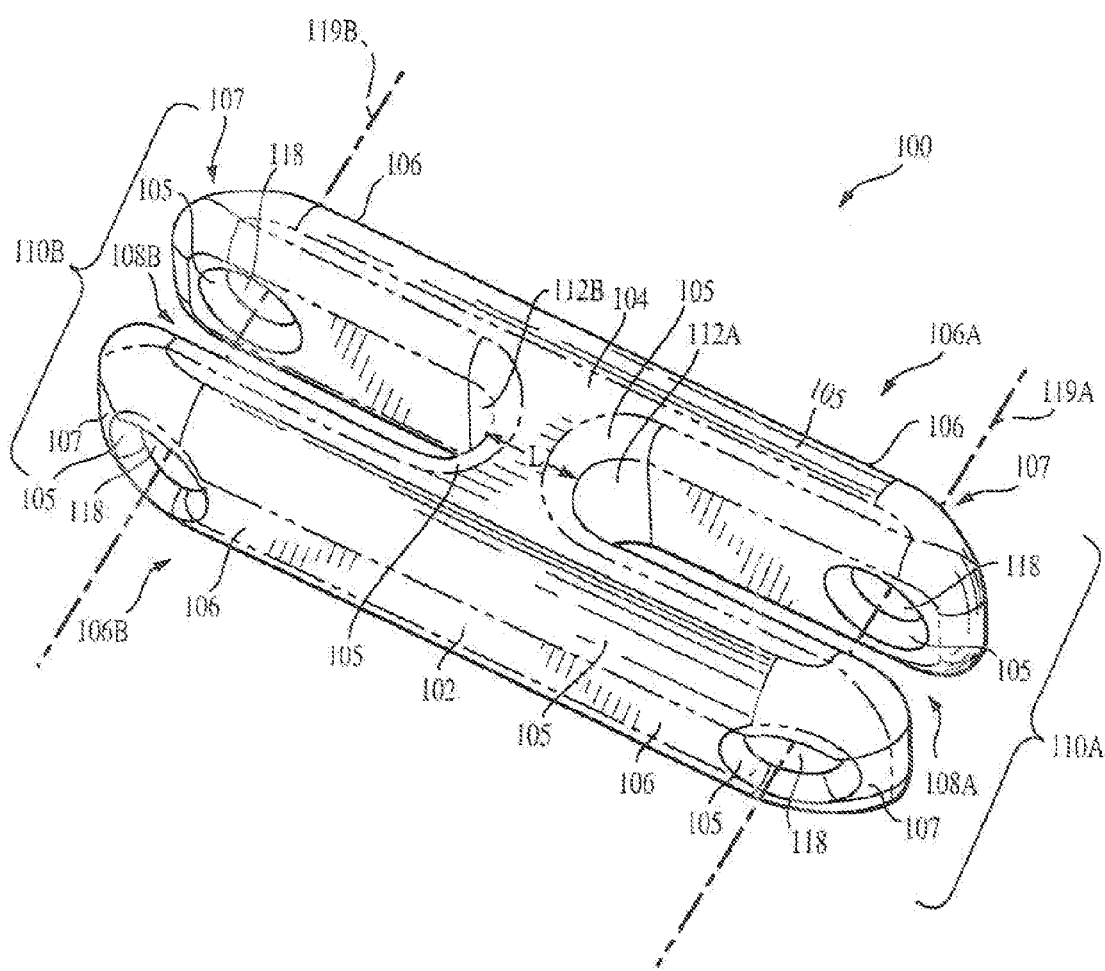
FIG. 2 is an example of the graft fixation member.

In one example, shown in FIG. 2, graft fixation member 100 has an elongated body 102 formed of biocompatible material (e.g. titanium or acetal) or a bioabsorbable material (e.g. polylactic acid, polyglycolic acid) with a length of about 0.45 inches, a width of about 0.16 inches, and a thickness of about 0.1 inches. Body 102 has a width allowing fixation member 100 to be pulled through tibial channel 16, femoral channel 14, and passing channel 18.

Body 102 includes an intermediate portion 104 having a length (L), which defines the distance between a pair of channels 108A, 108B at opposing ends body 102, described below. In one example, length (L) of intermediate portion 104 is about 0.05 inches. Intermediate portion 104 supports closed-loop suture 30 during implantation and bears the tension of closed-loop suture 30 after tissue graft 20 has been implanted.

Pairs of arms 106A and 106B extend from intermediate portion 104. Arms 106 have rounded edges 105 along their length and rounded ends 107. In one example, rounded edges 105 have a radius of about 0.015 inches and rounded ends 107 have a radius of about 0.067 inches. Rounded edges 105 allow fixation member 100 to be more easily pulled through tibial channel 16, femoral channel 14, and passing channel 18.

Channels 108A and 108B are formed by pairs of arms 106A and 106B, respectively. Channels 108A and 108B are open at end portions 110A and 110B of elongated body 102 and have cylindrical closed portions 112A and 112B formed by intermediate portion 104 and pairs of arms 106A and 106B, respectively. For example, cylindrical closed portions 112A and 112B could have a diameter of about 0.05 inches and channels 108 and 108B could have a corresponding width of about 0.05 inches. Open end portions 110A and 110B of channels 108A and 108B allow closed-loop suture 30 to pass into channels 108A and 108B as described below.

In this particular embodiment, each arm 106 has an opening 118 located toward the end of and extending through arm 106. Openings 118 are cylindrical and have a diameter of about 0.04 inches. Openings 118 in pair of arms 106A are disposed on a common axis 119A, which is transverse to the length of elongated member 102. Openings 118 in pair of arms 106B are disposed on a common axis 119B, which is also transverse to the length of elongated member 102. In other examples, openings 118 could be skewed in relation to each other or disposed at different positions along arms 106.

Figure 3:
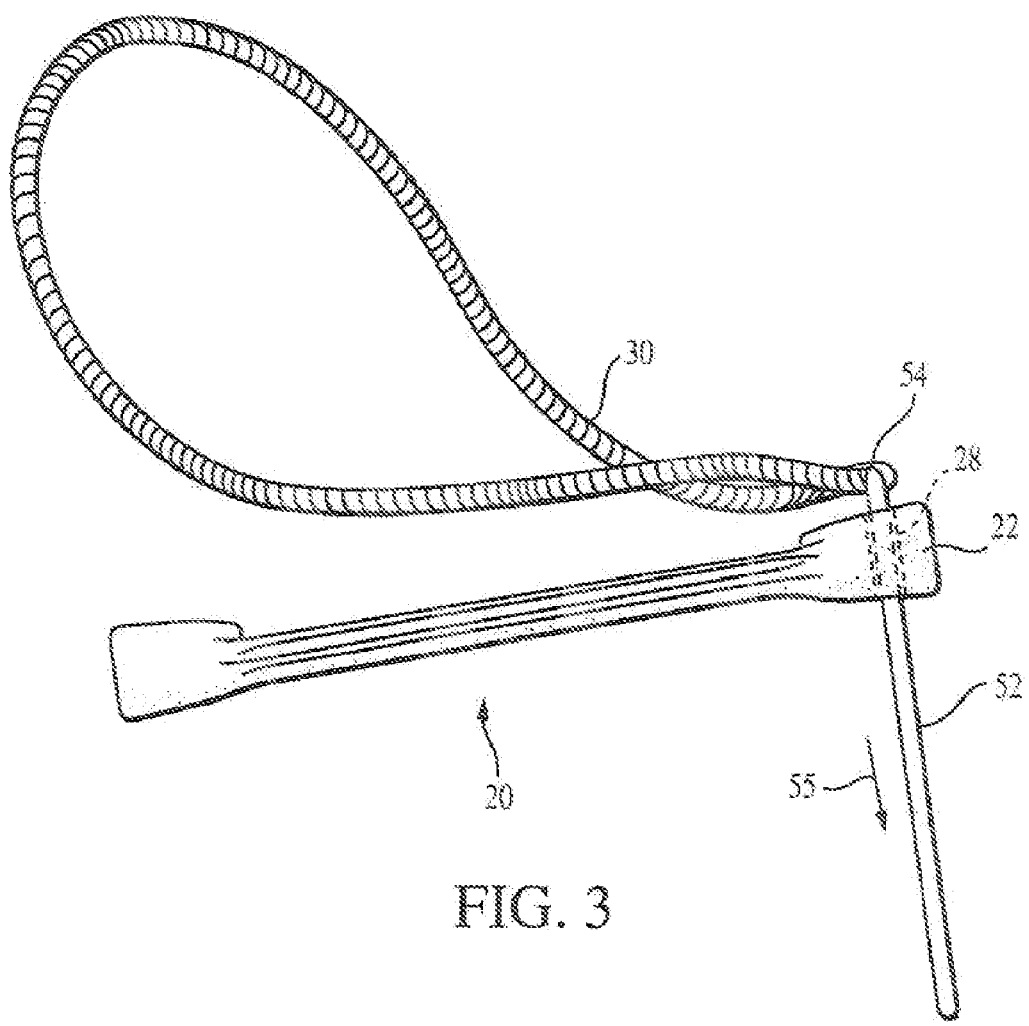
FIG. 3 shows an exploded partial view of how a closed-loop suture could be inserted into tissue graft.
Figure 4:
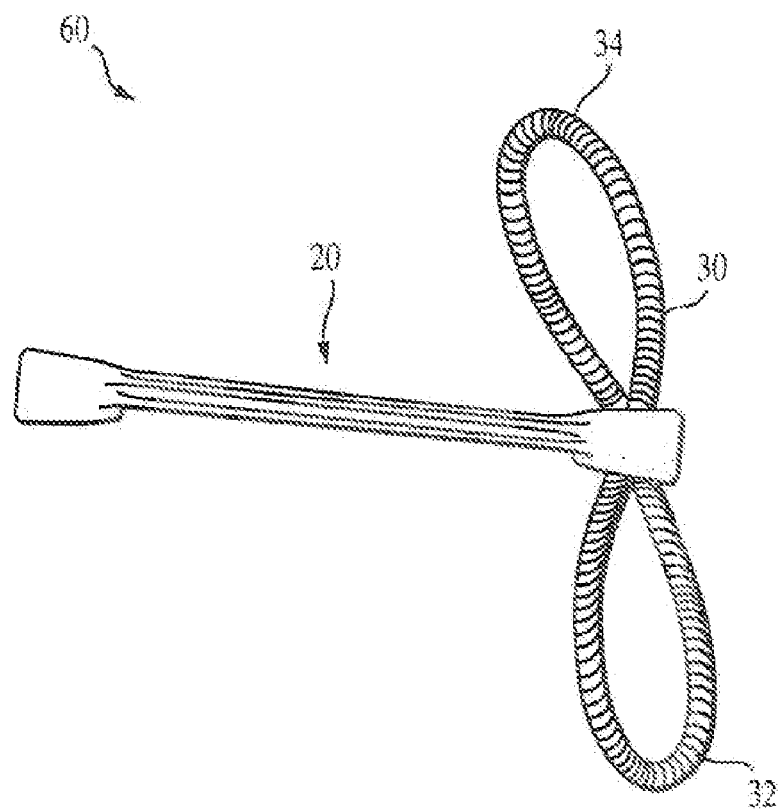
FIG. 4 is an example of a graft-loop assembly before being attached to the graft fixation member.

Referring to FIGS. 3-7, an example of a procedure for attaching graft fixation member 100 to tissue graft 20 follows. Referring to FIGS. 3 and 4, opening 28 is formed, for example, by drilling through bone block 22. A surgeon chooses a closed-loop suture 30 from closed-loops of several lengths to best position the tissue graft 20 within femoral channel 14 and tibial channel 16 (FIG. 1). The surgeon inserts suture grabber 52 into opening 28 until the end 54 of device 52 extends from bone block 22 and positions closed-loop suture 30 with suture grabber 52 and pulls both back through opening 28 in direction 62, forming a first bight 32 and a second bight 34 of about the same size on either side of bone block 22. Alternatively, a length of suture (not shown) could be used to pull closed-loop suture 30 into opening 28. One end of the suture could be passed through opening 28, through closed-loop suture 30, and back through opening 28. Closed-loop 30 may then be positioned in opening 28 by pulling both ends of the strand of suture.

Figure 5:
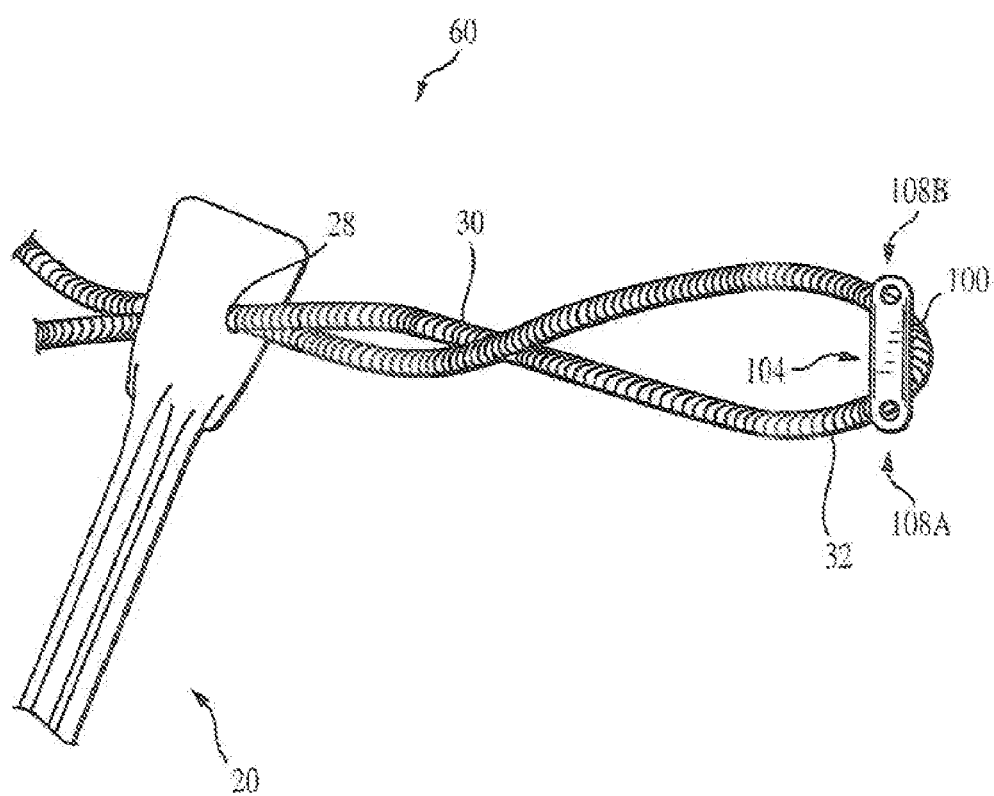
FIG. 5 shows an exploded partial view of a graft-loop assembly partially captured by the graft fixation member.
Figure 6:
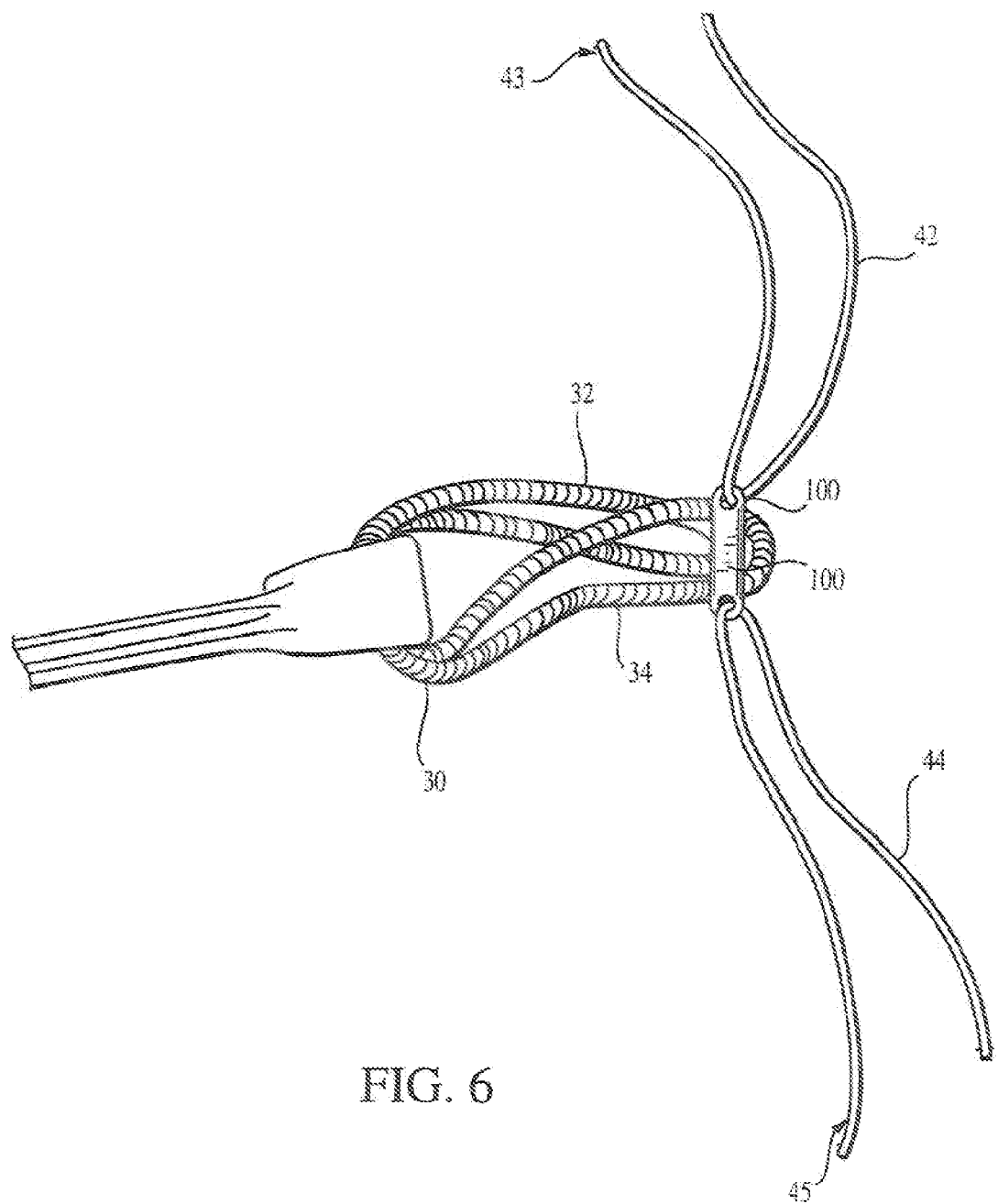
FIG. 6 shows an exploded partial view of a graft-loop assembly fully captured by the graft fixation member.

Referring to FIGS. 5 and 6, bight 32 is positioned around graft fixation member 100 and into channels 108A, 108B so that the continuous loop of suture 30 is wrapped around intermediate portion 104 of graft fixation member 100. Bight 34 of continuous loop suture 30 is then similarly positioned around graft fixation member 100 and into channels 108 so that the continuous loop of suture 30 wraps around intermediate member 104 of graft fixation member 100. Both bights 32, 34 are wrapped around intermediate member 104 so that the closed-loop suture 30 does not interfere with the positioning of strands of suture 42 into openings 118.

Lengths of suture 42 and 44, shown in FIG. 6, are chosen to capture closed-loop suture 30 within graft fixation member 100 during the ACL reconstruction described below. In one example, lengths of polyester closure tape could be used instead of sutures 42, 44. End 43 of suture 42 is passed through opening 118 (FIG. 2) in either arm 106 of pair of arms 106A and over closed-loop suture 30. End 43 is then passed through opening 118 in the corresponding arm 106 of pair of arms 106A thereby capturing closed-loop suture 30 within graft fixation member 100. It is important that suture 42 passes over, and not under, closed-loop suture 30. Allowing suture 42 to pass under closed-loop 30 would not capture closed-loop 30 within graft fixation member 100. Similarly, end 45 of suture 44 is passed through opening 118 in either arm 106 of pair of arms 106B and over closed-loop suture 30. End 45 is then passed through opening 118 in the capturing closed-loop suture 30. As was the case with suture 42, passing suture 44 under closed-loop 30 does not capture closed-loop 30 within graft fixation member 100. In this manner, closed-loop suture 30 is captured twice within fixation member 100.

Figure 7:
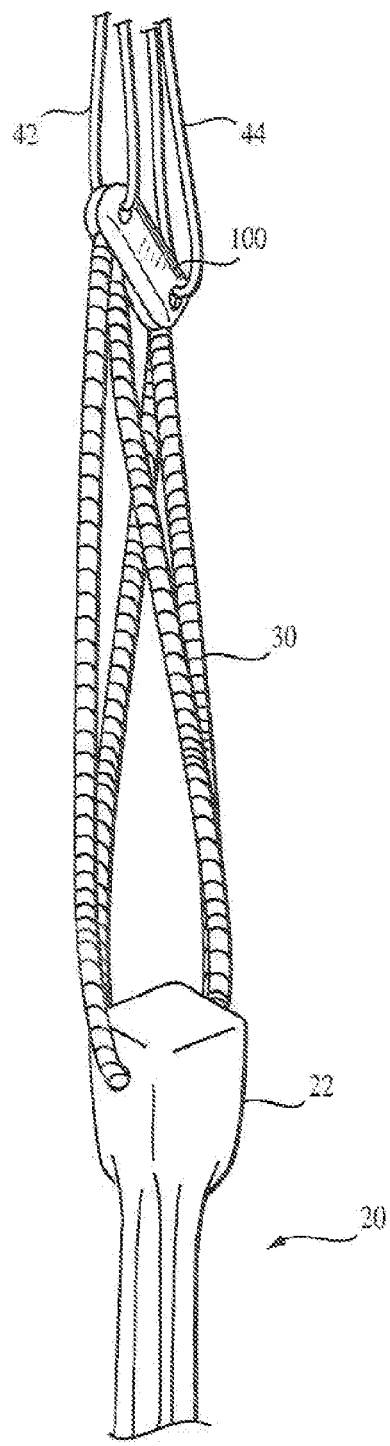
FIG. 7 shows the graft fixation member positioned for implantation.

Referring to FIG. 7, pulling to sutures 42 and 44 removes slack from closed-loop suture 30 and positions graft fixation member 100 to pass through tibial channel 16, femoral channel 14, and passing channel 18 (FIG. 2).

Figure 8:
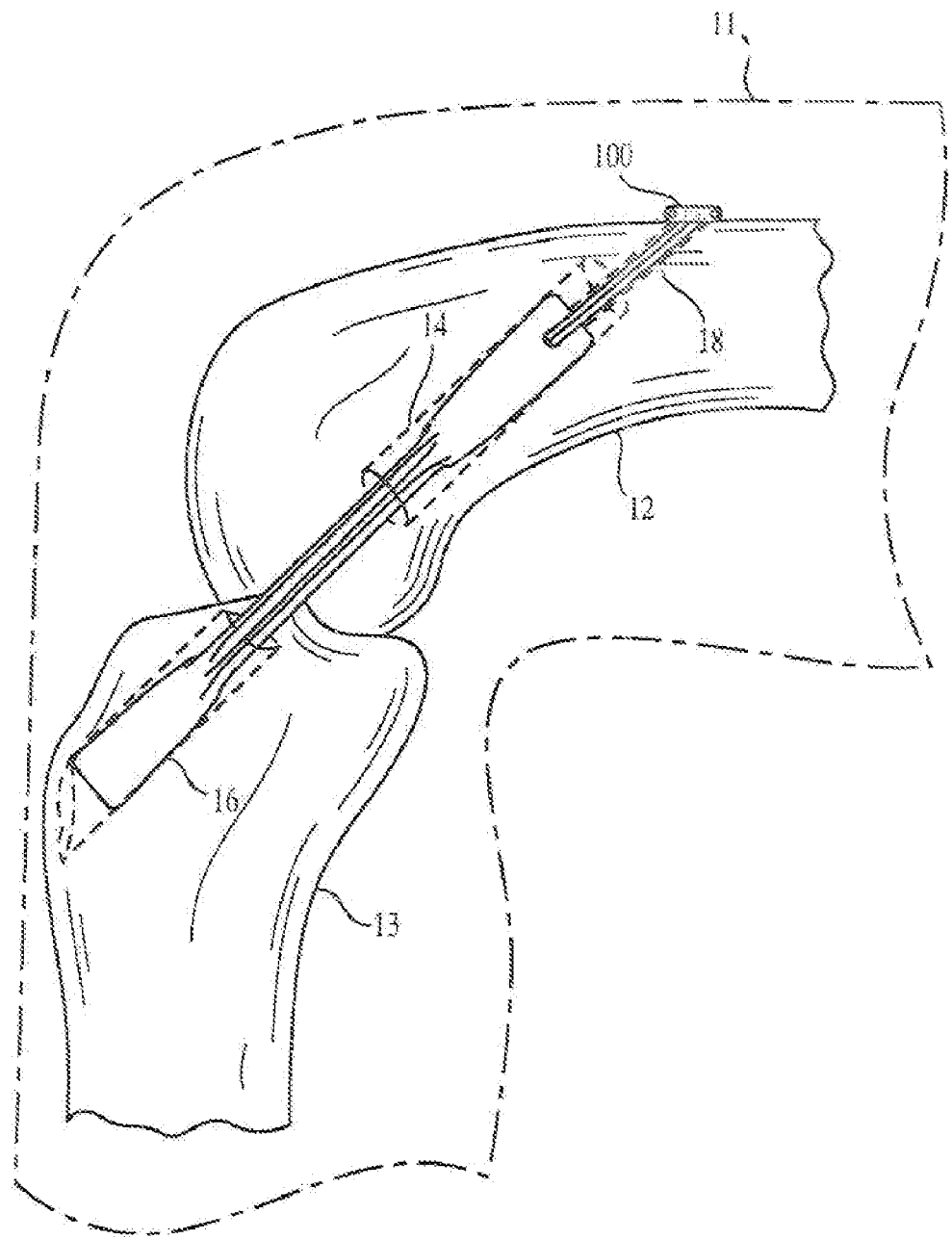
FIG. 8 shows the tissue graft implanted in a knee and secured at one end by the graft fixation member.

An example of a procedure for placing graft fixation member 100 in the position shown in FIG. 8 follows with reference to FIG. 1. Drilling procedures are performed to provide the appropriately sized tibial channel 16 extending through tibia 13 and femoral passage 14 in the manner described in the '301 patent. Sutures 42 and 44 are removably attached to passing pin 50. Passing pin 50 (FIG. 1) is then inserted through an incision below the knee and advanced through tibial channel 16, femoral channel 14, passing channel 18, the quadriceps tissue, and skin 11 of the thigh. Ends of sutures 42 and 44 are withdrawn beyond the skin 11 using passing pin 50.

The surgeon then pulls graft fixation member 100 by pulling suture 42 through tibial channel 16, femoral channel 14, and passing channel 18 to position graft fixation member 100. It is important that the surgeon keep closed-loop suture 30 captured within channel 108B by taking up any slack in suture 44 while advancing graft fixation member 100 through passing channel 18 with suture 42. However, the surgeon must be careful not to apply too much tension on suture 44 in relation to the tension on suture 42 or graft fixation member 100 will wedge within tibial channel 16, femoral channel 14, or passing channel 18. Once fixation member 100 has been pulled through passing channel 18, the surgeon positions fixation member 100 transversely to passing channel 18 and across opening 19. Fixation member 100 is secured against femur 12 by attaching tissue graft 20 to tibia 13 and tensioning tissue graft 20 and closed-loop suture 30 according to methods described in the '301 patent.

Other embodiments are within the scope of the claims.

Figure 9:
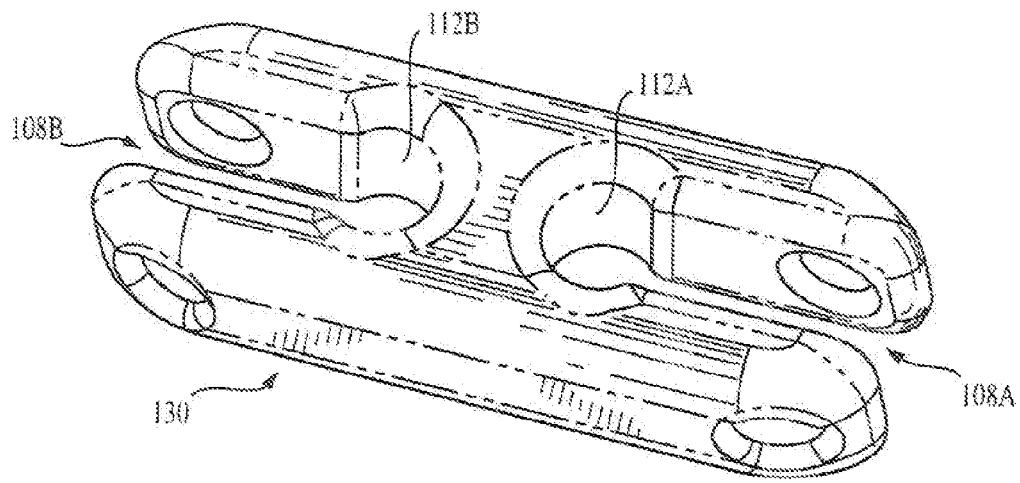
FIG. 9 shows an alternative example of a graft fixation member.

For example, referring to FIG. 9, cylindrical portions 112A and 112B of graft fixation member 130 may have a diameter that is larger than the width of channels 108A and 108B, respectively. In one example, portions 112A, 112B have a diameter of about 0.078 inches and channels 108A, 108B have a width of about 0.05 inches. As the diameter of portions 112A and 112B increases, graft fixation member 100 can accommodate a thicker closed-loop suture (i.e. having an increased number of windings). The width of channels 108A and 108B do not constrain the sue of thicker closed-loop sutures because a closed-loop suture may be flattened to pass through channels 108A and 108B.

Figure 10:
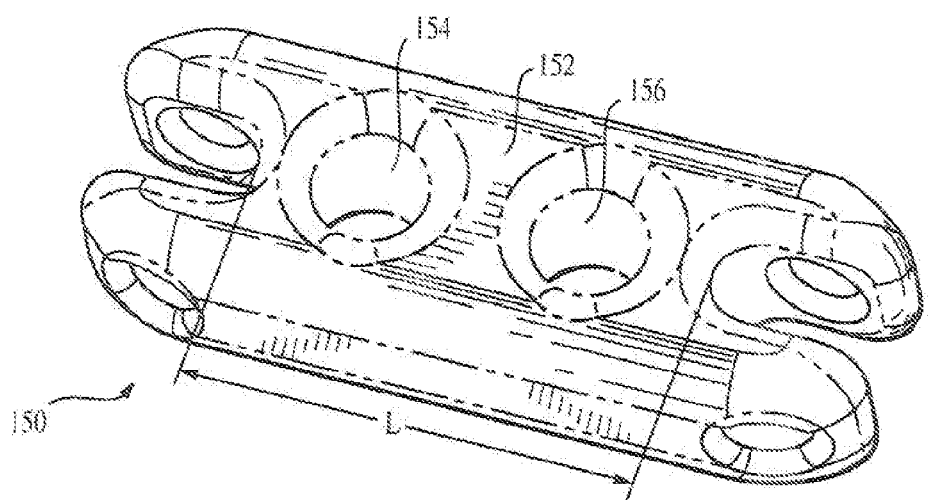
FIG. 10 shows a second alternative example of a graft fixation member.
Figure 11:
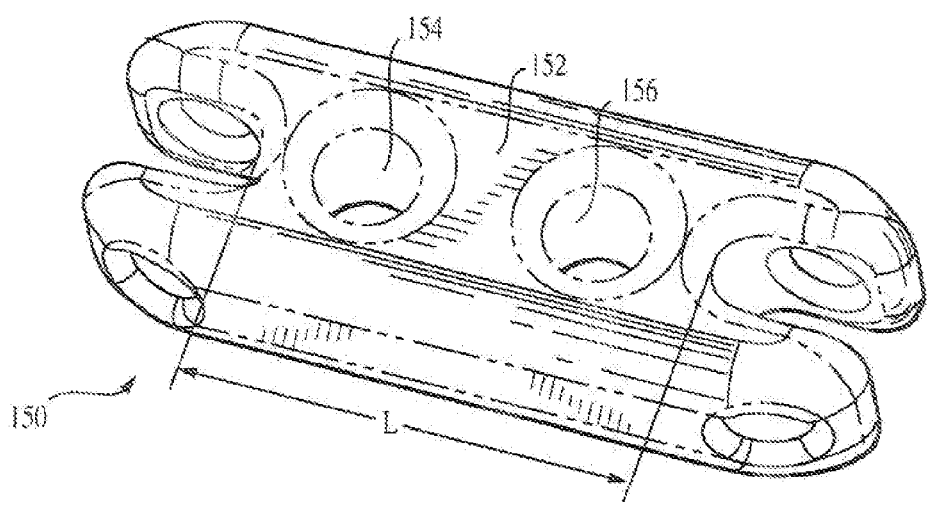
FIG. 11 shows a third alternative example of a graft fixation member.

Referring to FIGS. 10 and 11, intermediate portion 152 of fixation member 150 has a length (L) and defines openings 154, 156 extending through intermediate portion 152. In the example shown in FIG. 10, intermediate portion has a length of about 0.268 inches and openings 154, 156 are about 0.078 inches in diameter. In the example shown in FIG. 11, intermediate portion has a length of about 0.232 inches and openings 154, 156 are about 0.06 inches in diameter. A closed-loop suture 30 may be attached to fixation member 150 using the method described in the '079 application. Alternatively a first and second end of a length of suture or closure tape may be threaded through openings 154, 156, respectively, and tied together. Increasing length L adds material to intermediate portion 152 and increases the strength of graft fixation member 150.

Figure 12:
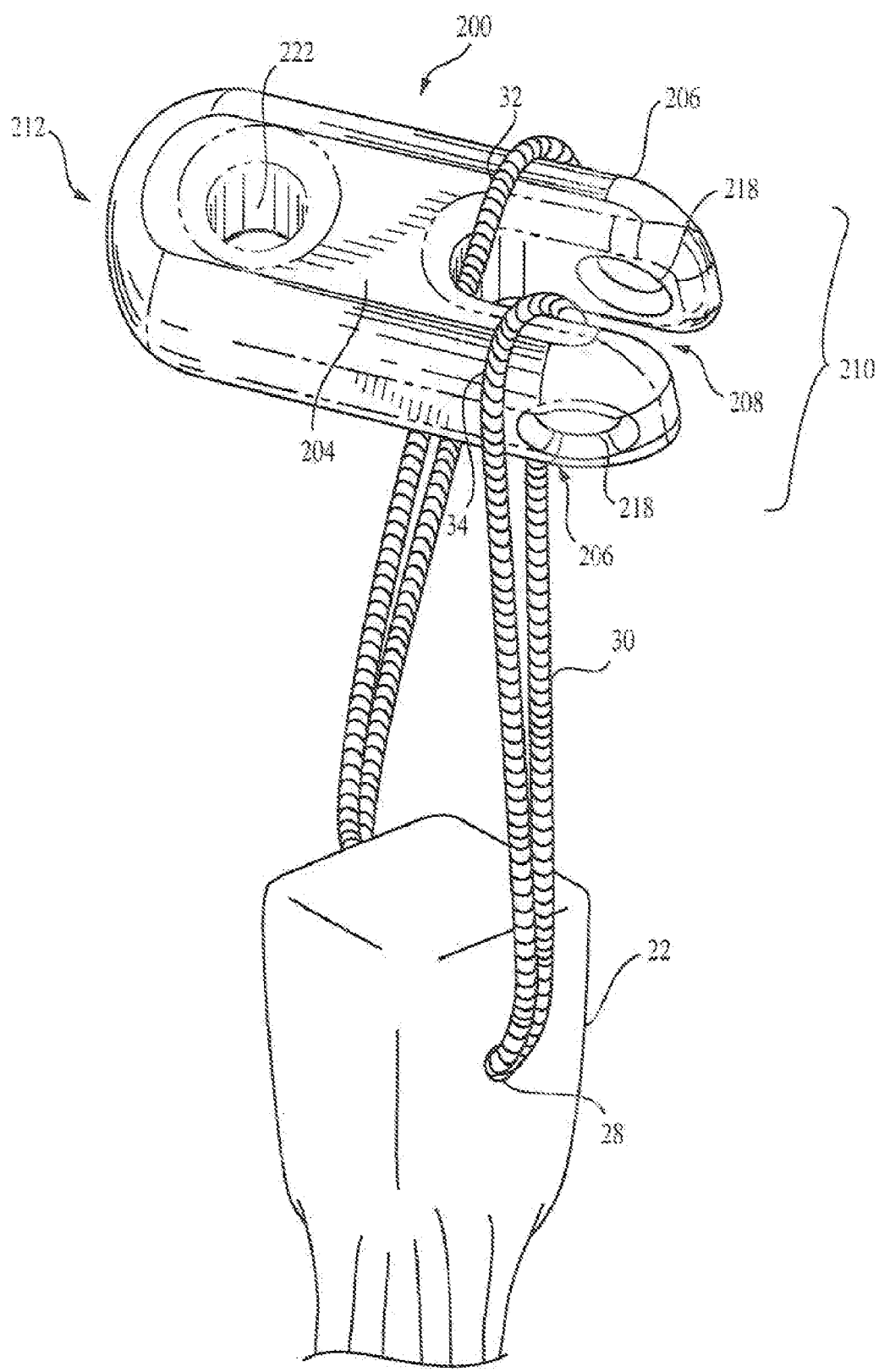
FIG. 12 shows a fourth alternative example of a graft fixation member and a method for capturing first and second portions of a closed-loop suture.

Referring to FIG. 12, fixation member 200 has only one pair of arms 206 extending from intermediate portion 204 and forming a single channel 208 at end 210. Arms 206 include cylindrical openings for capturing closed-loop suture 30 and positioning fixation member 200. End 212 is closed and rounded to facilitate passing fixation member 200 through bone passages during the positioning and attachment of tissue graft 20. End 212 may include opening 222 through which a strand of suture may be threaded to improve a surgeon's ability to position fixation member 200 during an ACL reconstruction procedure.

Closed-loop suture 30 is captured in fixation member 200 by positioning arms 206 through bights 32, 34 and threading suture 42 (not shown) through a first opening 218, over bights 32, 34, and through the second opening 218. In one example, bight 32 is positioned on a first arm 206 and bight 34 is positioned on a second arm 206. In another example, bights 32, 34 could be positioned on the same arm.

Figure 13:
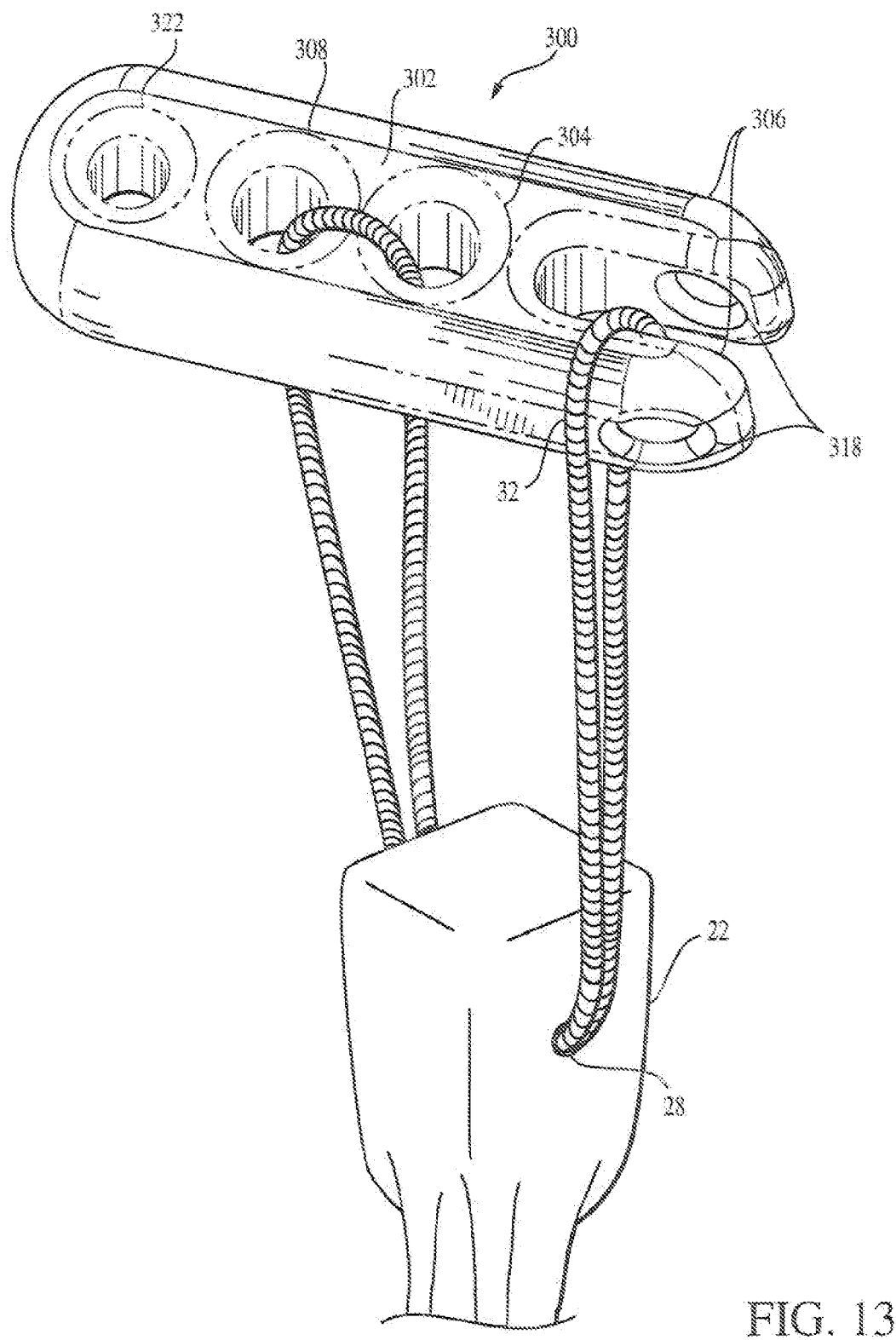
FIG. 13 shows a fifth alternative example of a graft fixation member and a method of attaching it to a tissue graft using a closed-loop suture.

Referring to FIG. 13, fixation member 300 includes openings 304, 308, an intermediate portion 302 and a pair of arms 306 with an opening 318 through each arm. Closed-loop suture 30 is formed in openings 304, 308 according to the method described in the '079 application. Alternatively, a piece of suture or closure tape could be tied into a loop passing through openings 304, 308 as described above. After forming bight 32 by passing closed-loop suture 30 into opening 28 in bone block 22, closed-loop suture 30 is captured by fixation member 300 by positioning either arm 306 through bight 32 and threading a strand of suture (not shown) through openings 318, as described above.

Figure 14:
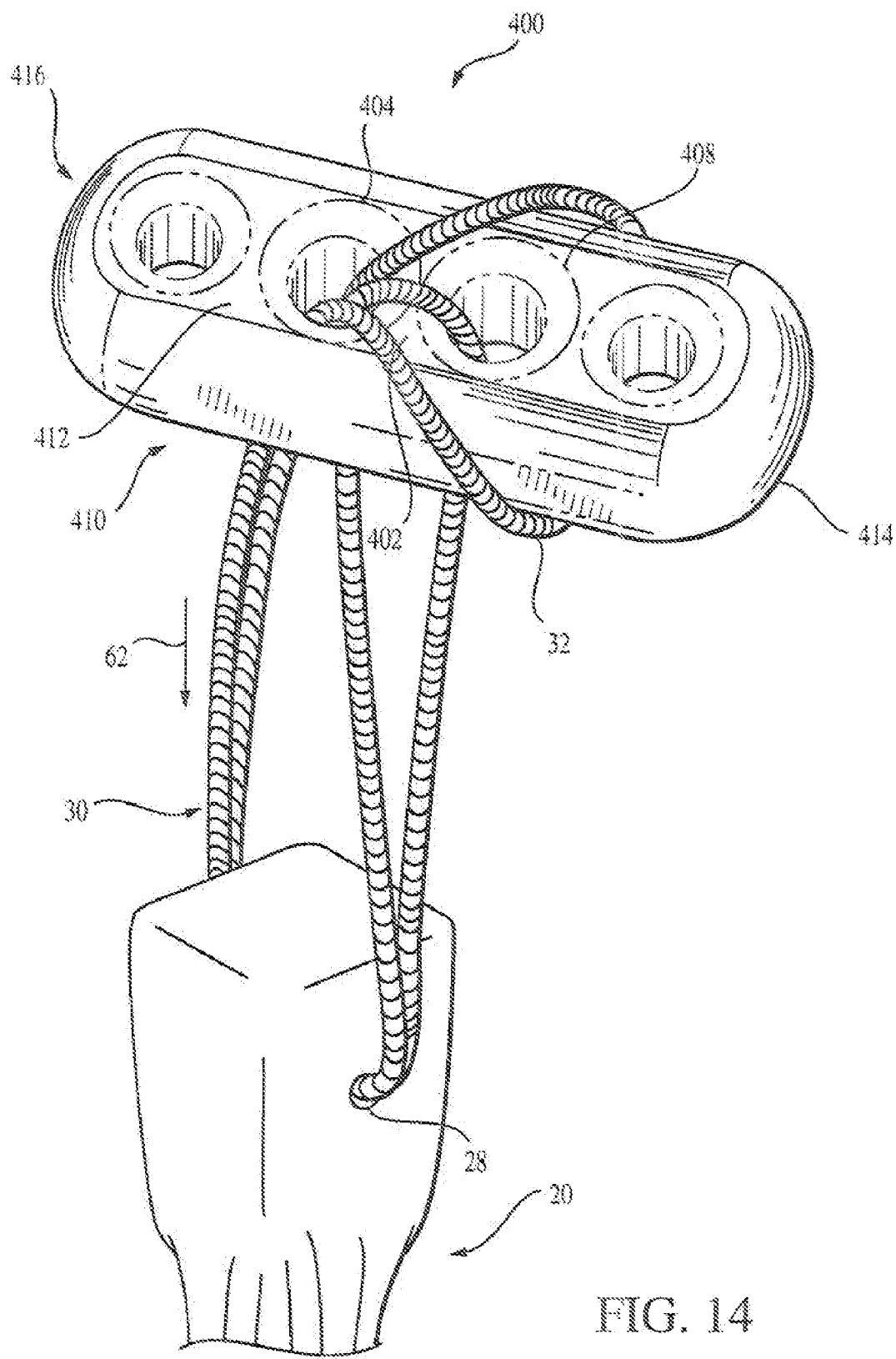
FIG. 14 shows a sixth alternative example of a graft fixation member and method of attaching it to a tissue graft using a closed-loop suture.

Referring to FIG. 14, fixation member 400 is similar in size to fixation member 100, described above, and has a four opening configuration described in the '301 and '894 patents. Closed-loop suture 30 has been formed in openings 404, 408 of fixation member 400 according to the method set forth in the '079 patent, thereby capturing a first portion of closed-loop suture 30.

Tissue graft 20 is attached to fixation member 400 by passing closed-loop suture 30 into opening 28, thereby forming bight 32, and capturing a second portion of closed-loop suture 30 with fixation member 400. In the example of FIG. 14, bight 32 is inserted into opening 404 at bottom side of member 400 and out of opening 404 at top side 412 until bight 332 can extend past end 414 of fixation member 400. End 414 is passed through bight 32. Bight 32 is pulled in direction 62 until bight 32 tightens around fixation member 400, thereby capturing a second portion of closed-loop suture 30. In another example, end 416 could be passed through bight 32 instead of end 414.

Figure 16:
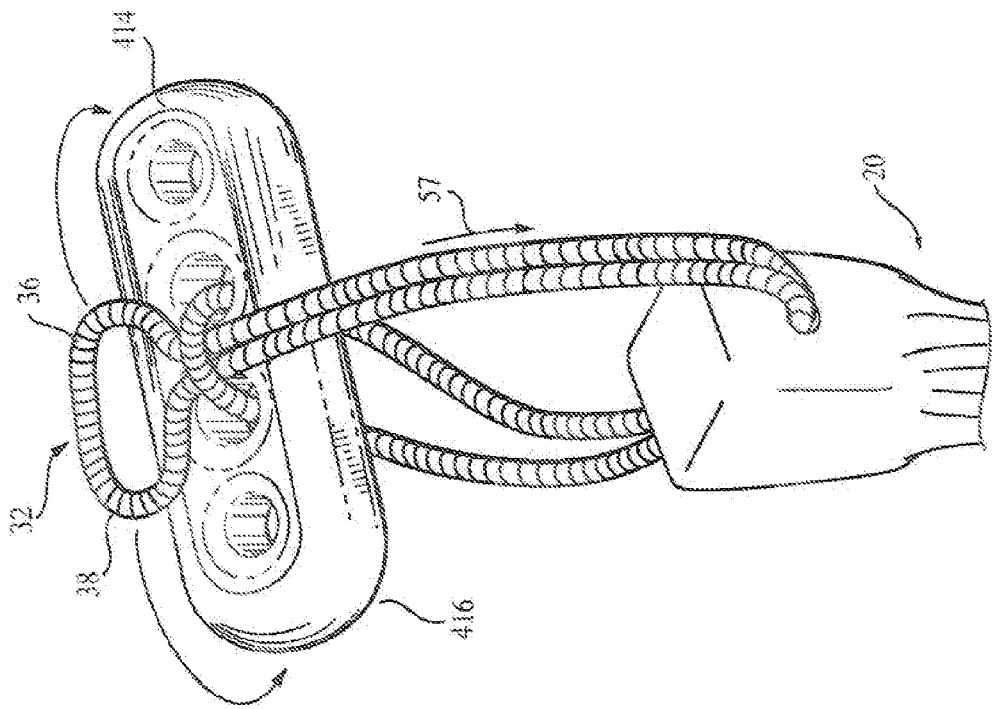
FIGS. 15-17 show an alternative method for attaching a graft fixation member to a tissue graft using a closed-loop suture.
Figure 15:
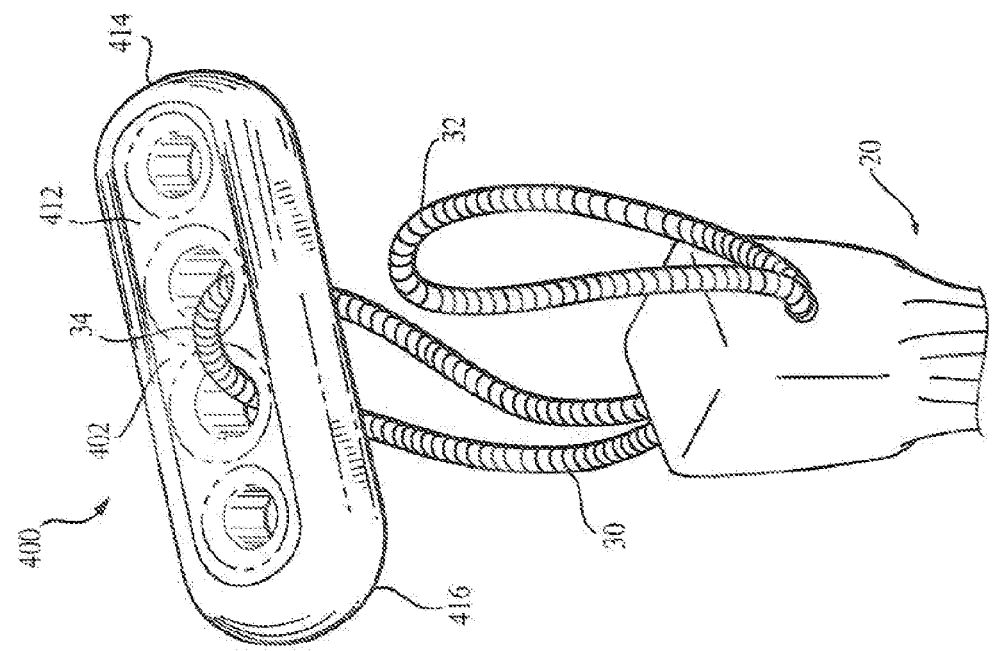
Figure 17:
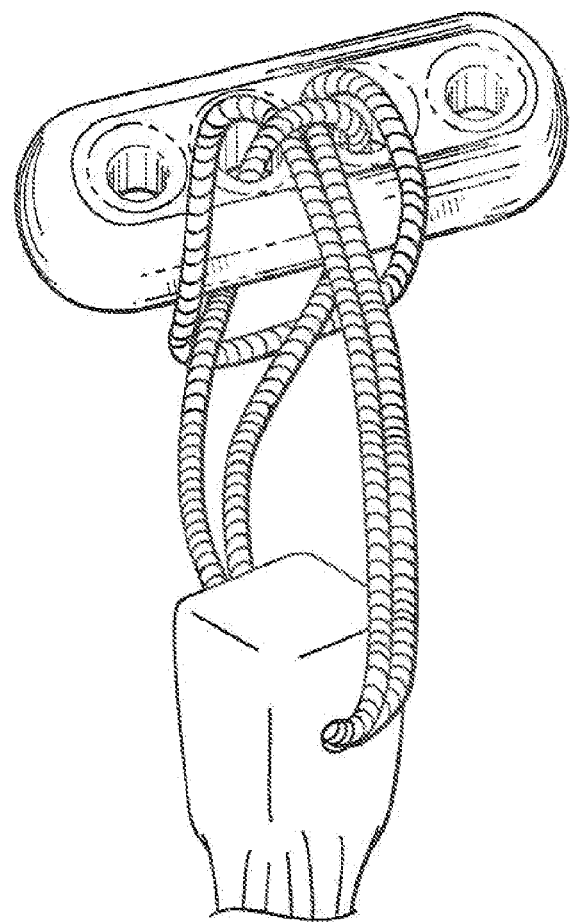

Referring to FIGS. 15-17, another method by which tissue graft 20 could be attached to fixation member 400 follows. Closed-loop suture 30 has been formed around intermediate portion 402 of fixation member 400 according to the method described in the '079 application and a portion of closed-loop suture 30 is passed into opening 28, as described above, to form bights 32, 34. Bight 32 is passed through bight 34 on top side 412 of fixation member 400; about 1 inch of closed-loop suture 30 has been pulled through bight 34. Bight 32 is then opened to form bights 36, 38; end 414 is then passed through bight 36, and bight 28 is passed through end 416. Closed-loop suture 30 is tensioned in direction 57, removing slack from closed-loop suture 30 and attaching it to fixation member 400.

Figures 18A, 18B, 18C, 18D:
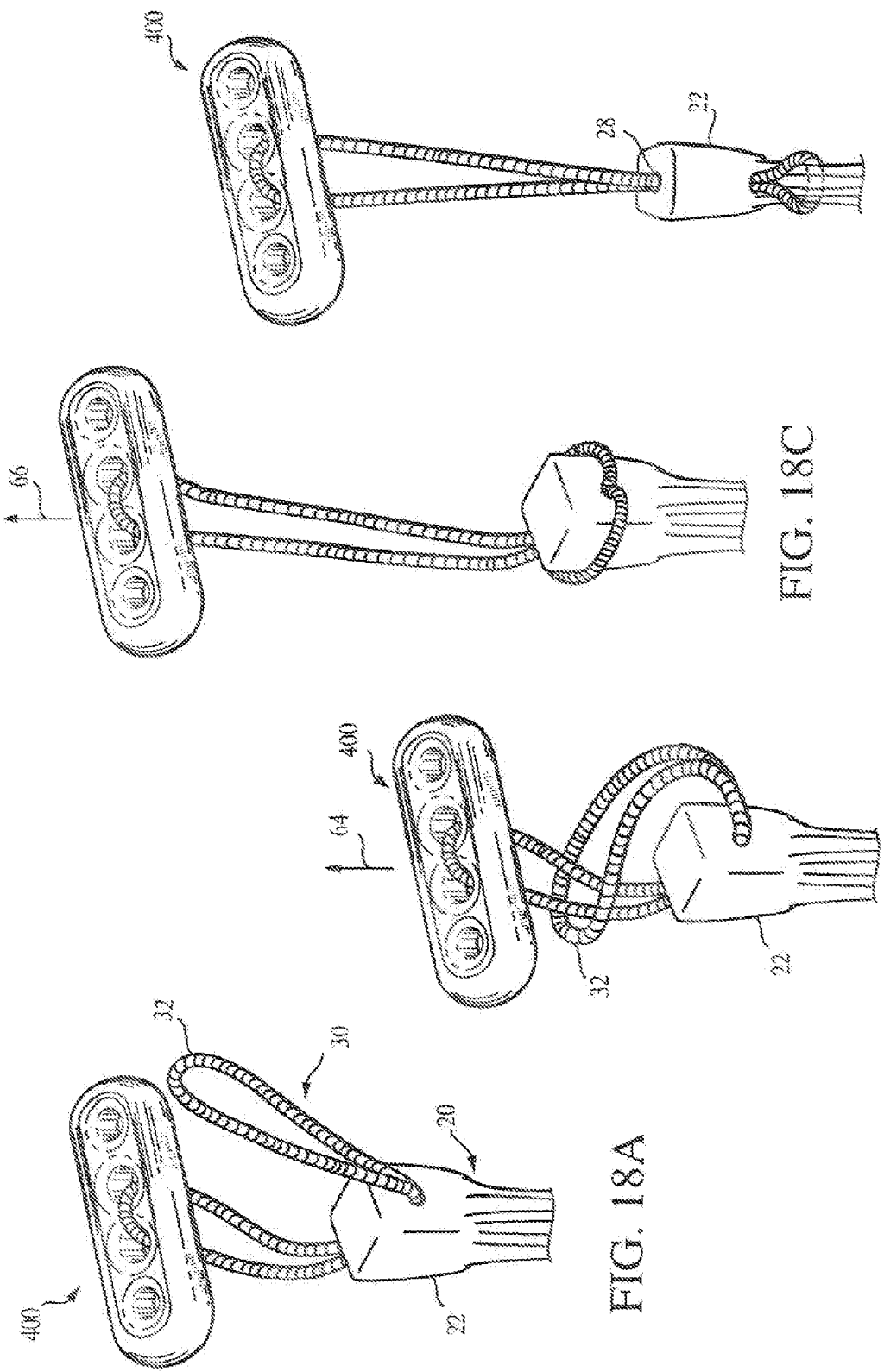
FIGS. 18A-18D show a second alternative method for attaching a graft fixation member to a tissue graft using a closed-loop suture.

Referring to FIGS. 18A-D, tissue graft 20 could be attached to fixation member 400 by capturing closed-loop suture 30 only once at fixation member 400. For example, closed-loop 30 is passed through opening 28 (not shown) in bone block 22 to form bight 32 (FIG. 18A). Fixation member 400 is then passed through bight 32 (FIG. 18B) and pulled in direction 66, away from tissue graft 20, thereby causing bight 32 to tighten around bone block 22, as best seen in FIG. 18C. In another embodiment, opening 28 is formed along the length of block 22 (FIG. 18D) instead of transversely, as shown in examples above. Fixation member 400 is attached to tissue graft 20 in the same manner as described above despite the longitudinal orientation of opening 28.

Figure 19:
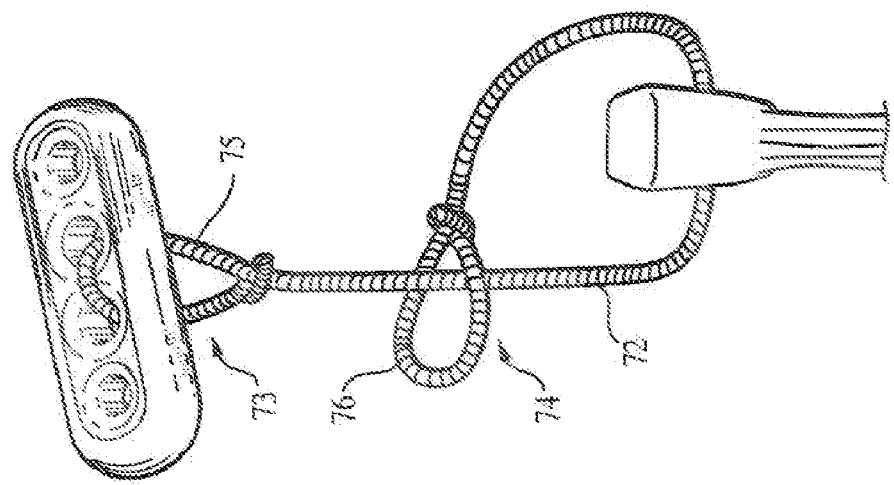
FIG. 19 shows an alternative example of a closed-loop suture.

Referring to FIG. 19, closed-loop suture 70 is a suture 72 having opposing ends 73 and 74. In one example, suture 72 could have a total length of about 1.5 inches. End 73 includes a loop 75, and end 74 includes a loop 76. Loops 75, 76 have a length of about 0.3 inches or less.

Figure 20:
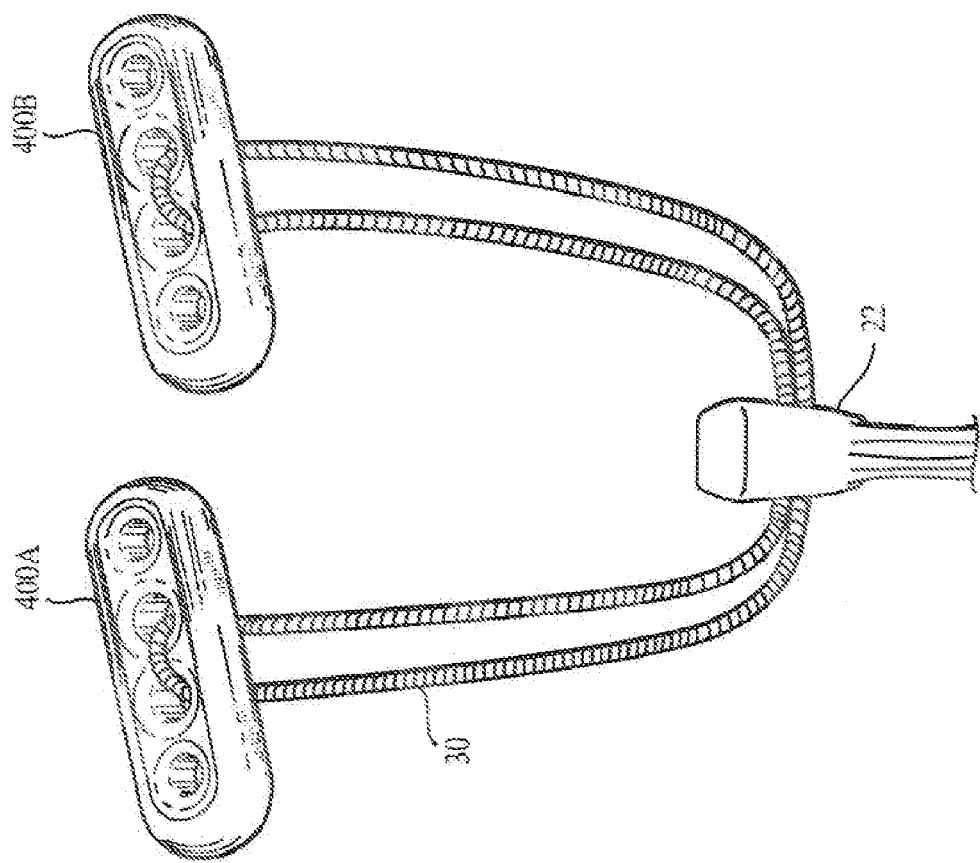
FIG. 20 shows a third alternative method for attaching a graft fixation member to a tissue graft using a closed-loop suture.

Referring to FIG. 20, a closed-loop suture 230 is formed in more than one fixation member 400. In one example, closed-loop suture 230 is formed in fixation member 400A and 400B. When closed-loop suture 230 is formed by the method disclosed in the '079 application, opening 28 (not shown) in bone block 22 is sized to permit fixation member 400 to pass through opening 28. When closed-loop suture 230 is formed by tying a length of suture or closure tape, opening 28 need only be sized to accommodate the suture or tape. During implantation, a surgeon could use sutures (e.g. suture 42, 44) to pass fixation members 400A, 400B through passing channel 18 at the same time or pass them individually.

Figure 21A:
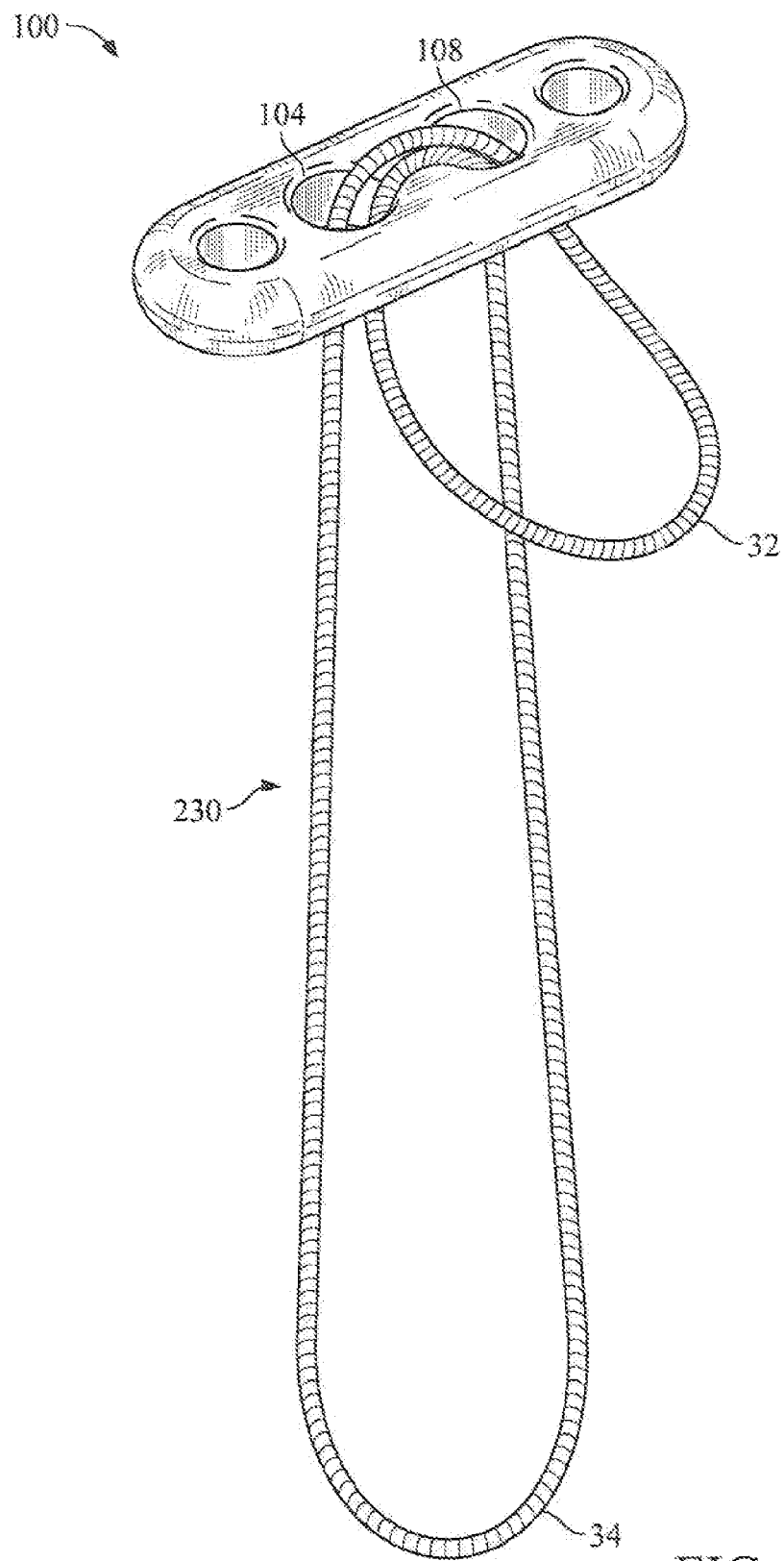
FIG. 21A is an example of the closed double-loop captured in the graft fixation member having a pair of closed-loop sections.

Tissue graft may also include a closed-double loop formed of the same suture described above. Referring to FIG. 21A, fixation member 100 has a four opening configuration as described FIG. 14. In this embodiment, the closed-loop is a continuous loop 230 passed twice through openings 104, 108 forming two differently sized loop ends 32, 34. Loop 230 is captured in fixation member 100. An advantage of a continuous closed-loop is the even distribution of the load when the loop is passed through the graft.

Figure 21B:
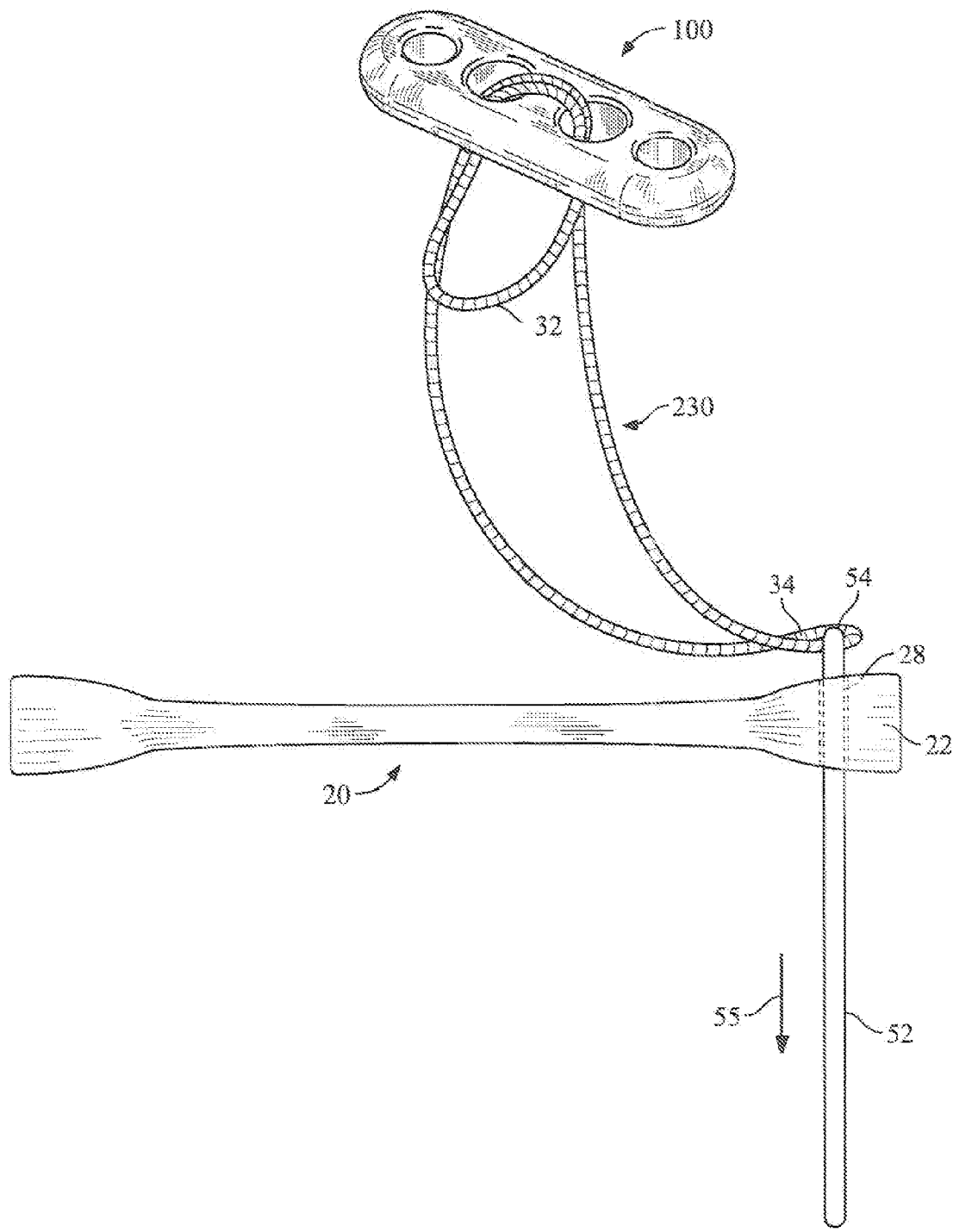
FIG. 21B shows an exploded partial view of how the longer end of the closed double-loop suture could be inserted into the tissue graft.
Figure 21C:
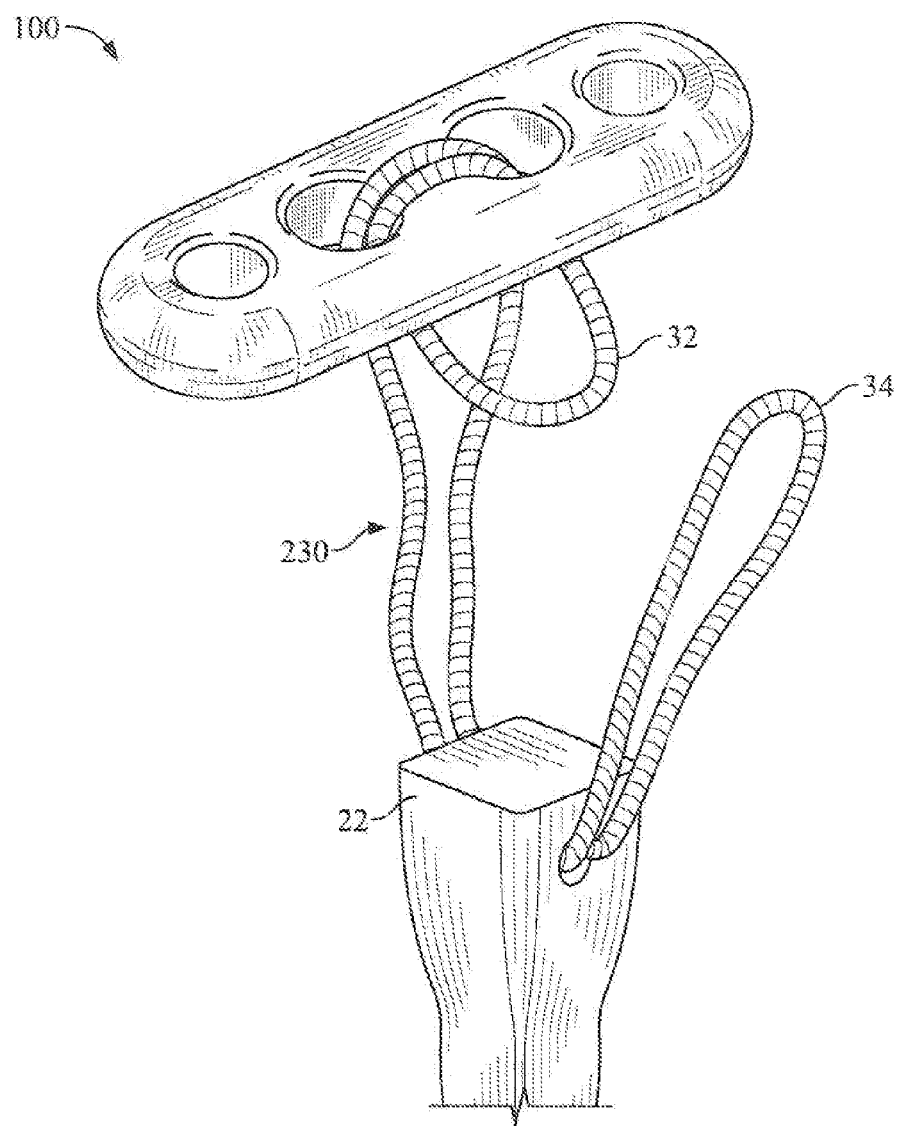
FIGS. 21C-21F show a method of tying the knot to secure the graft fixation member and closed double-loop to the tissue graft.

Referring to FIG. 21B, continuous loop 230 is attached to bone block 22, for example, by drilling an opening 28 through bone block 22. A surgeon chooses an appropriate closed-loop suture 230 (with fixation member 100) from closed-loops of several lengths to best position the tissue graft 20 within femoral channel 14 and tibial channel 16 (FIG. 1). The surgeon inserts suture grabber 52 into opening 28 until the end 54 of device 52 extends from bone block 22 and closed-loop suture end 34 is then positioned next to bone block 22. The surgeon grabs closed-loop suture end 34 with suture grabber 52 and pulls both through opening 28 in direction 55, leaving loop end 34 on one side of bone block 22. Graft fixation member 100 and loop end 32 are on the other side of bone block 22 as shown in FIG. 21C.

Alternatively, a length of suture (not shown) could be used instead of a suture grabber to pull closed-loop suture end 34 into opening 28. One end of the suture could be passed through opening 28, through closed-loop suture 230, and back through opening 28. Closed-loop 230 may then be positioned in opening 28 by pulling both ends of the strand of suture.

Figure 21D:
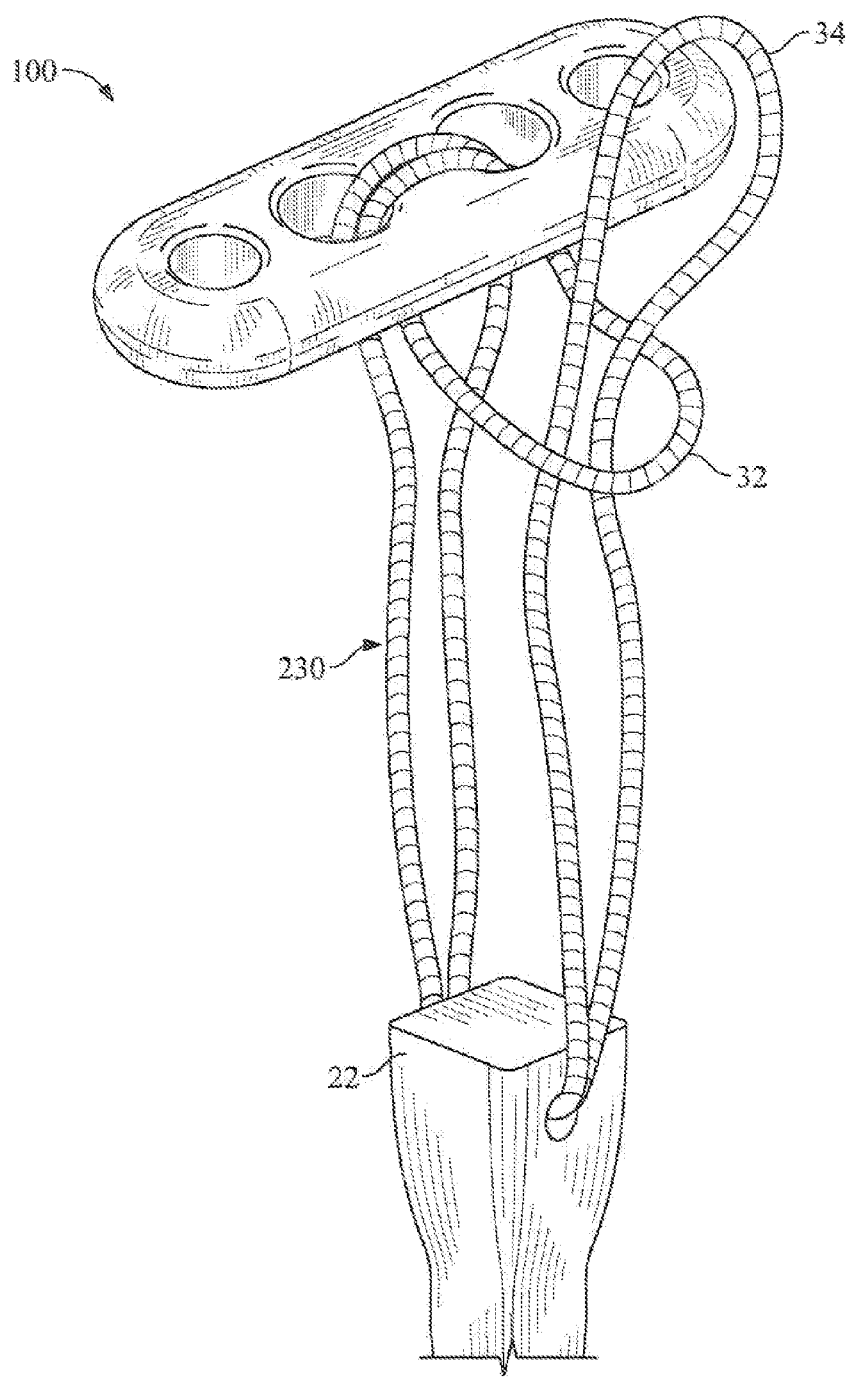
Figure 21E:
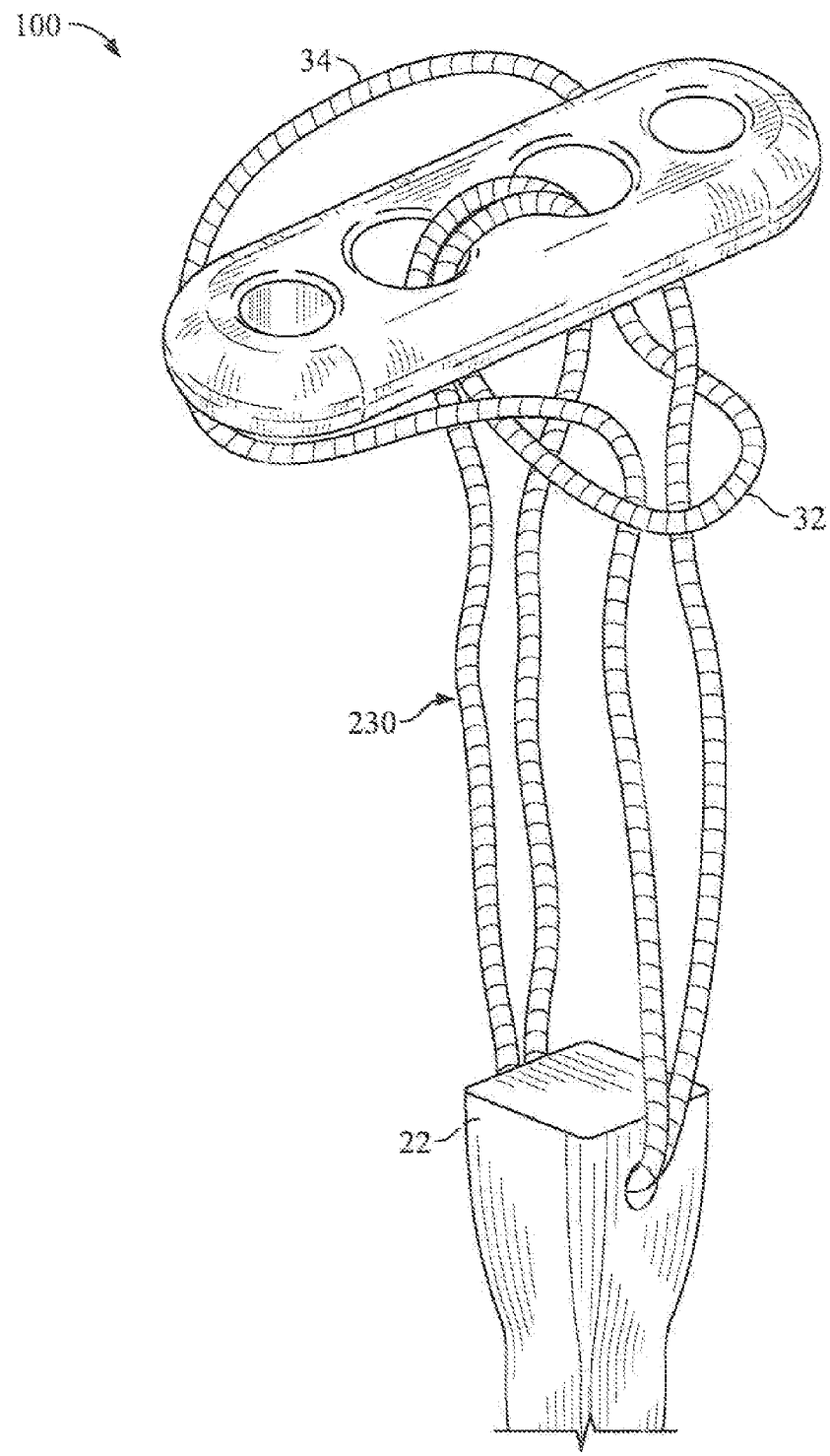
Figure 21F:
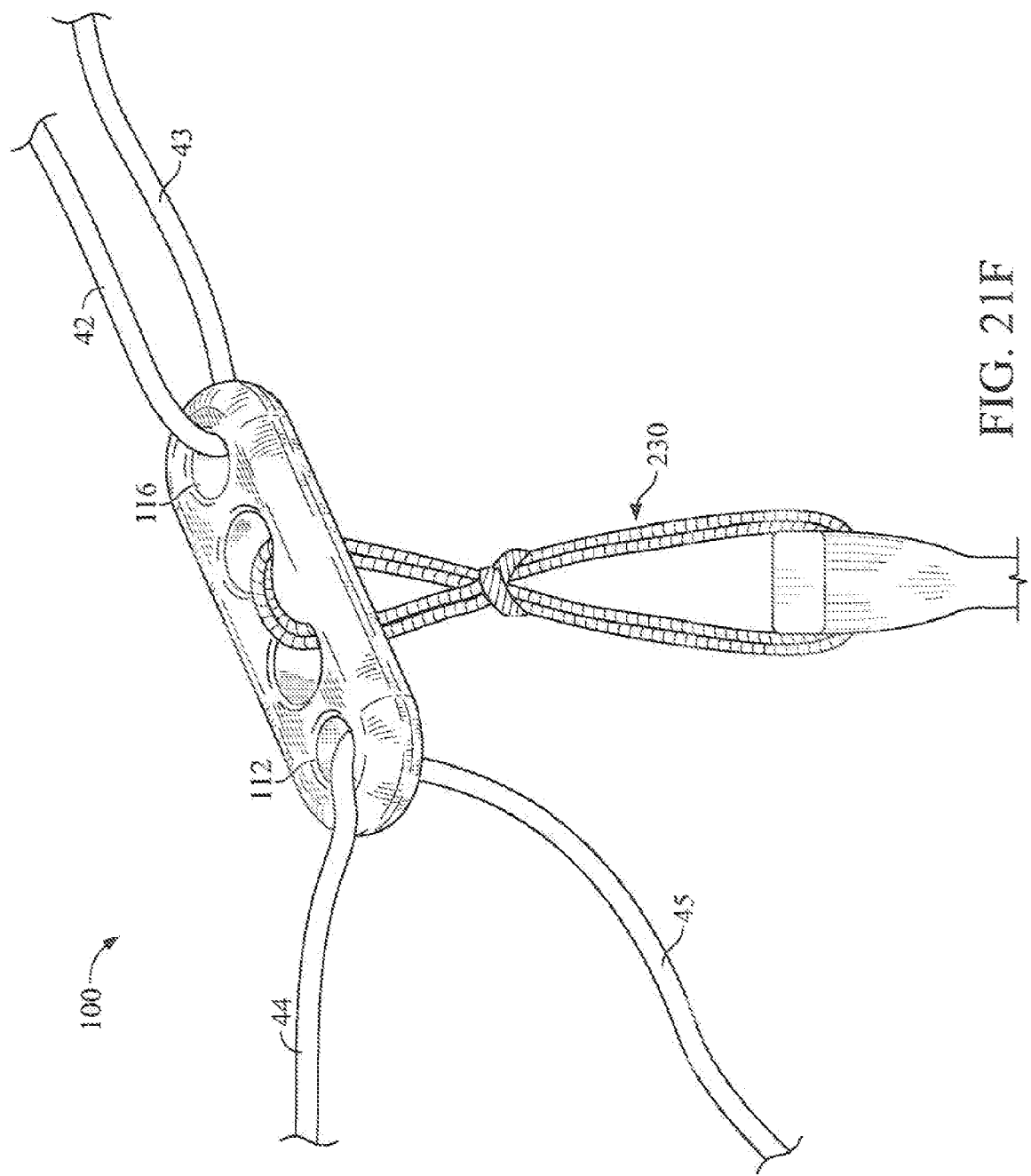

In FIG. 21D, loop end 34 is passed under loop end 32 and pulled above graft fixation member 100. In FIG. 21E, loop end 34 is opened sufficiently wide to pass over graft fixation member 100. In FIG. 21F, graft fixation member 100 is pulled tight from bone block 22, causing a knot to form in closed-loop 30, thereby capturing the bone block 22 with the closed-loop 230 and graft fixation member 100. The small section of the closed-loop dictates where the knot lies with the knot preferably positioned close to the graft fixation member.

Lengths of suture 42 and 44 are passed through respective holes 116, 112 of fixation member 100. Sutures 42, 44 are used to position graft fixation member 100 during the ACL reconstruction described below. In one example, lengths of polyester closure tape could be used instead of sutures 42, 44. End 43 of suture 42 is passed through opening 116. End 45 of suture 44 is passed though opening 112.

Figure 21G:
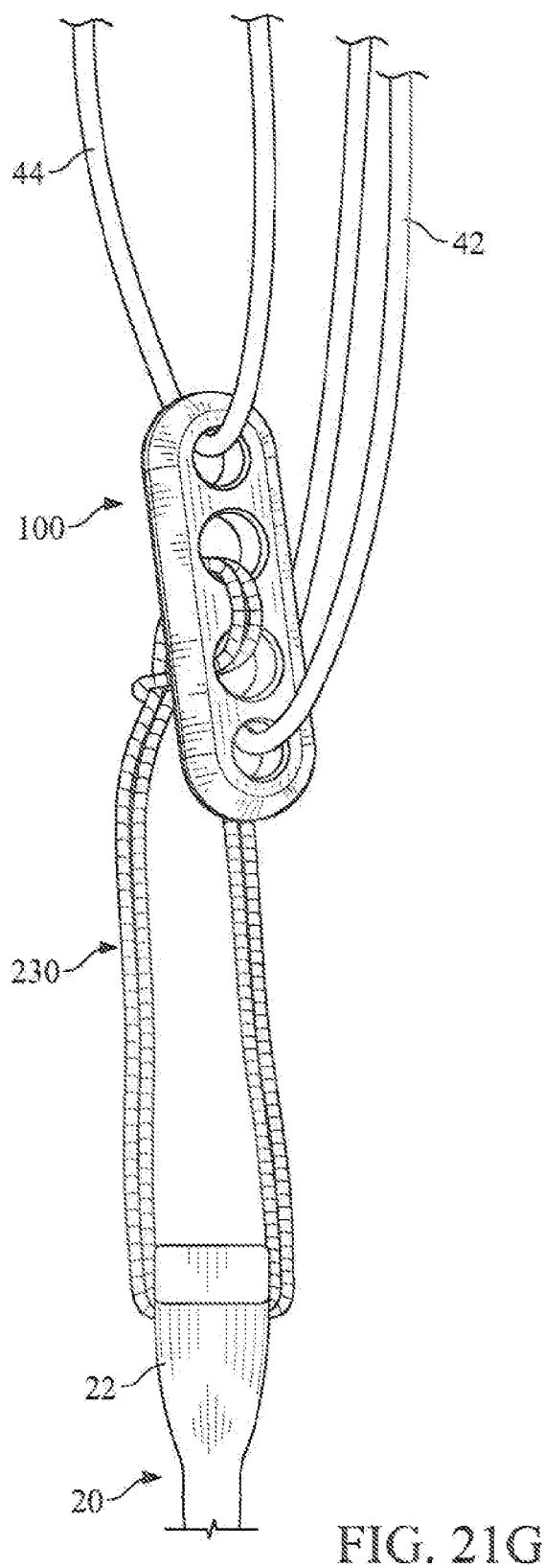
FIG. 21G shows the graft fixation member positioned for implantation.

Referring to FIG. 21G, pulling sutures 42 and 44 removes slack from closed-loop suture 30 and places graft fixation member 100 and loop 230 in a position for passing through tibial channel 16, femoral channel 14, and passing channel 18 (FIG. 1).

As discussed above in conjunction with FIG. 8, the surgeon then pulls graft fixation member 100 by pulling suture 42 through tibial channel 16, femoral channel 14, and passing channel 18 to position graft fixation member 100.

Once fixation member 100 has been pulled through passing channel 18, the surgeon positions fixation member 100 transversely to passing channel 18 and across opening 19. Fixation member 100 is secured against femur 12 by attaching tissue graft 20 to tibia 13 and tensioning tissue graft 20 and closed-loop suture 30 according to methods described in the '301 patent.

Figure 22:
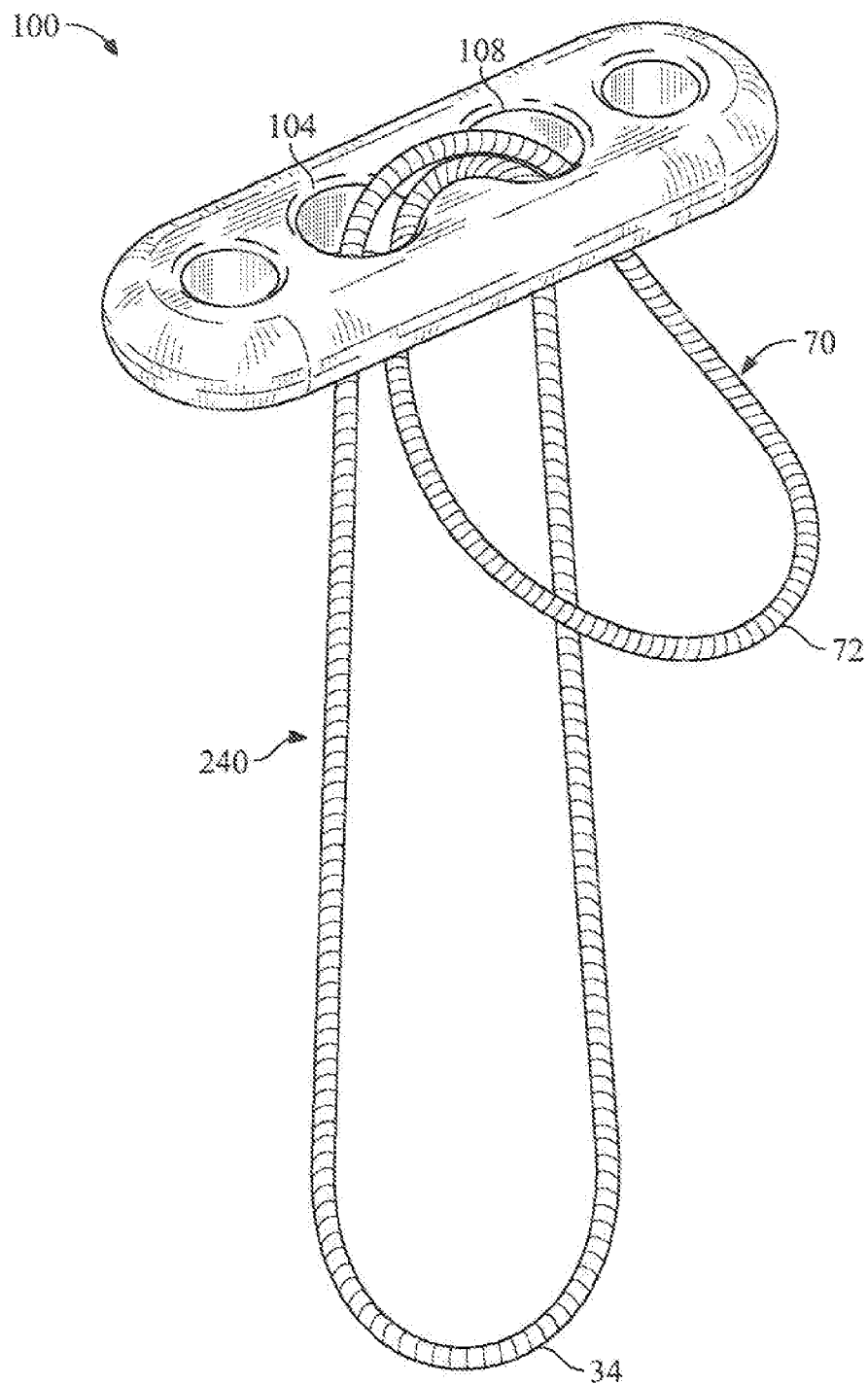
FIG. 22 is an example of the closed double-loop captured in the graft fixation member having a pair of closed-loop sections.
Figure 23:
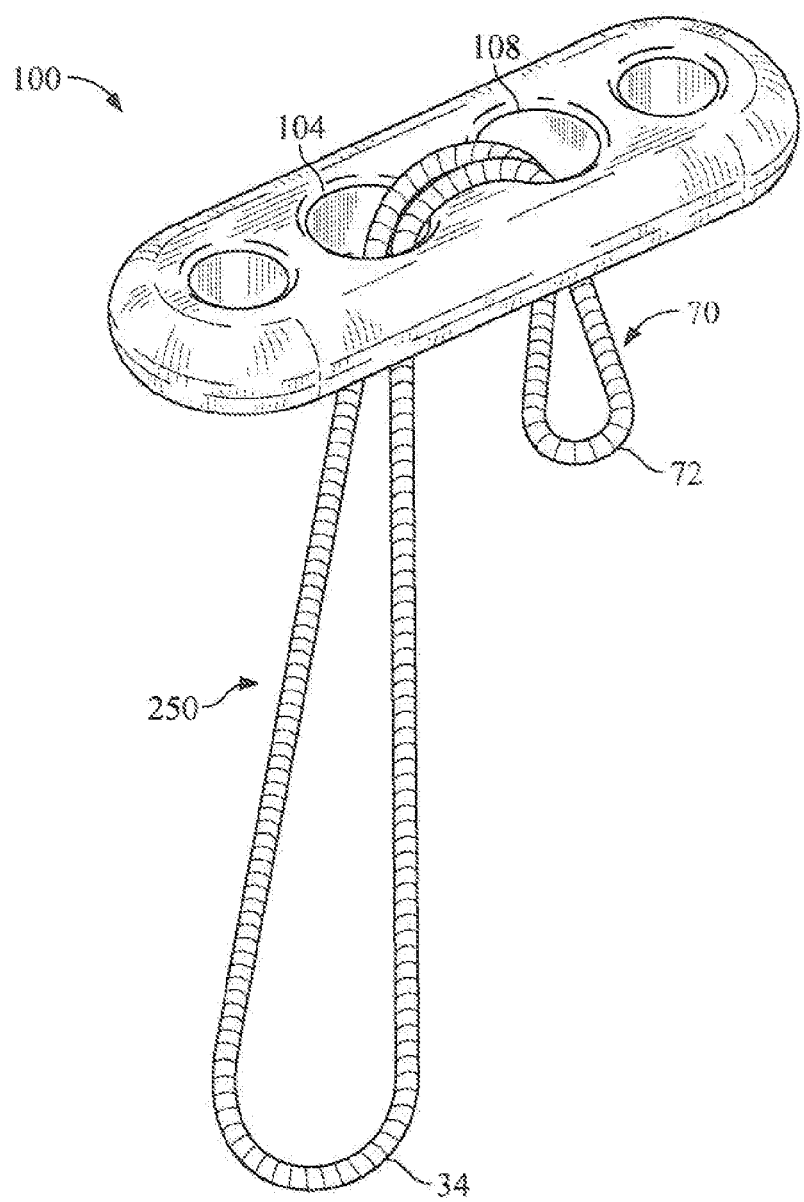
FIG. 23 is a second example of the closed double-loop captured in the graft fixation member having a pair of closed-loop sections.

Alternative embodiments of the invention include those shown in FIGS. 22 and 23. In FIG. 22, loop end 72 of closed-loop 230 is passed through opening 104, then passed though opening 108. The loop is not captured, but is held to fixation member 100. In FIG. 23, two differently sized closed-loops 230, 70 are formed in openings 104, 108 of fixation member 100 according to the method set forth in the '079 patent. Both closed-loops are captured in fixation member 100. Loop ends 34, 72 are used in the method of fixation through knotting in the same manner as loop ends 34, 32 are for the devices described in FIG. 21.

Other embodiments include an alternative approach for securing a tissue graft within a bone passage using fixation member 100. Specifically, the fixation member 100 and tissue graft 20 could be pulled first through a femoral channel and then through a tibial channel.

Although the tissue graft described above has at least one bone block, other types of grafts may be attached to graft fixation member including ligament augmentation devices (LAD) formed of artificial ligament material to which the tissue is sutured.

In general, the knot tying method using graft fixation member 100 in combination with closed double-loop 30 can be used to secure any suitable kinds of grafts, such as allografts, autografts, and xenografts, and can be used in surgical soft tissue reconstruction procedures other than those related to ACL reconstruction.

Accordingly, other embodiments are within the scope of the following claims.

What is claimed is:

1. A method of securing a tissue graft within a bone passage comprising:
   providing a graft fixation member comprising a closed double-loop having a pair of loop sections,
   capturing each of the pair of loop sections within the fixation member
   passing a first one of the sections through an opening in the tissue graft,
   passing the first one of the loop sections through a second one of the loop sections, and
   positioning the first loop section over the fixation member to form a knot.

2. The method of claim 1 in which the first loop section is longer than the second.

3. The method of claim 2 further comprising forming the opening in the tissue graft.

4. The method of claim 3 wherein the opening is formed in a bone block of the tissue graft.

5. The method of claim 3 wherein the opening is formed in a tendon of the tissue graft.

6. The method of claim 2 further comprising passing the fixation member through the bone passage.

7. The method of claim 6 wherein passing the fixation member through the bone passage comprises first passing the fixation member through a bone passage in a tibia and then through a bone passage in a femur.

8. The method of claim 6 wherein passing the fixation member through the bone passage comprises first passing the fixation member through a bone passage in a femur and then through a bone passage in a tibia.

9. The method of claim 1 further comprising positioning the fixation member to pass through the bone passage using a suture.

10. The method of claim 1 further comprising positioning the fixation member to pass through the bone passage using closure tape.

* * * * *